US007645917B2

(12) United States Patent
Cheah et al.

(10) Patent No.: US 7,645,917 B2
(45) Date of Patent: Jan. 12, 2010

(54) MUTANT MICE COMPRISING A MUTATED TYPE II PROCOLLAGEN ALPHA-1

(75) Inventors: Kathryn Song-Eng Cheah, Hong Kong (HK); Janet Chyng-Jiau Lin Zhang, Pokfulam (HK)

(73) Assignee: The University of Hong Kong, Hong Kong (CN)

( * ) Notice: Subject to any disclaimer, the term of this patent is extended or adjusted under 35 U.S.C. 154(b) by 0 days.

(21) Appl. No.: 11/187,160

(22) Filed: Jul. 22, 2005

(65) Prior Publication Data
US 2006/0031953 A1 Feb. 9, 2006

Related U.S. Application Data

(60) Provisional application No. 60/591,935, filed on Jul. 26, 2004.

(51) Int. Cl.
*A01K 67/027* (2006.01)
*G01N 33/00* (2006.01)
*C12N 15/00* (2006.01)
(52) U.S. Cl. .............................. 800/18; 800/3; 800/21
(58) Field of Classification Search .................... 800/3, 800/18, 21
See application file for complete search history.

(56) References Cited

U.S. PATENT DOCUMENTS 5,663,482 A * 9/1997 Prockop et al. ................ 800/3
6,472,170 B1 * 10/2002 Yang et al. ................. 435/69.1

OTHER PUBLICATIONS

Wheeler, VR et al. Pediatr Pathol 8(1):55-64, 1988.*
Suigmund, CD. Arterioscler Thromb Vasc Biol 20:1425-1429, 2000.*
Cameron, ER. Mol Biotech 7(3):253-65, 1997.*
Wall, RJ Theriogenology 45:57-66, 1996.*
Houdebine, LM. J Biotech 34:269-87, 1994.*
Mullins, JJ and LJ Mullins Hypertension 22:630-633, 1993.*
Mullinslj and JJ Mullins. J Clin Invest 8:S37, 1996.*
Kappel, CA et al Current Opinion in Biotech 3:548-553, 1992.*
Neimann, H. Trans Res 7:73-75, 1998.*
Lodish, H et al. Molecular Cell Biology, 4$^{th}$ ed. New York: W.H. Freeman & Co. Chapter 8.5, p. 1-8 of printout and Figure 8-35. The chapter was obtained from http://www.ncbi.nlm.nih.gov/books/bv.fcgi?highlight=transgenic,loxP,cre&rid=mcb.section.1965. printed on Aug. 2, 2007.*
Zheng, Z. et al., "Sudden Cardiac Death in the United States, 1989 to 1998," Circulation, 2001, 2158-2163, vol. 104.
Maron, B. et al., "ACC/ESC Expert Consensus Document," Journal of the American College of Cardiology, 2003, 1687-1713, vol. 42, No. 9.
Maron, B., "Sudden Death in Young Athletes," The New England Journal of Medicine, 2003, 1064-1075, vol. 349.
Fatkin, D. and Graham, R., "Molecular Mechanisms of Inherited Cardiomyopathies," Physiol. Rev., 2002, 945-980, vol. 82.

Rahkonen, O. et al, "Expression Patterns of Cartilage Collagens and Sox9 During Mouse Heart Development," Histochem. Cell. Biol., 2003, 103-110, vol. 120.
Potocki, L., et al. "Cardiac Malformation in Two Infants with Hypochondrogenesis," American Journal of Medical Genetics, 1995, 295-299, vol. 59.
Zhu, Y. et al., "Type IIA Procollagen Containing the Cysteine-rich Amino Propeptide is Deposited in . . . ," The Journal of Cell Biology, 1999, 1069-1080, vol. 144, No. 5.
Shi, Y. and Massague, J., "Mechanisms of TGF-β Signaling from Cell Membrane to the Nucleus," Cell, 2003, 685-700, vol. 113.
Zwijsen, A. et al., "New Intracellular Components of Bone Morphogenetic Protein/Smad Signaling Cascades," FEBS Letters, 2003, 133-139, vol. 546.
Keyes, W. et al., "Expression and Function of Bone Morphogenetic Proteins in the Development . . . ," Anat. Embroyol., 2003, 135-147, vol. 207.
Atkinson, C. et al., "Primary Pulmonary Hypertension is Associated with Reduced Pulmonary Vascular . . . ," Circulation, 2002, 1672-1678, vol. 105.
Schlange, T. et al., "BMP2 is Required for Early Heart Development During a Distinct Time Period," Mechanisms of Development, 2000, 259-270, vol. 91.
Ghosh-Choudhury, N. et al., "BMP-2 Regulates Cardiomyocyte Contractility in a Phosphatidylinositol 3 Kinase-Dependent Manner," FEBS Letters, 2003, 181-184, vol. 544.
Machado, R. et al., "BMPR2 Haploinsufficiency as the Inherited Molecular Mechanism for Primary Pulmonary Hypertension," Am. J. Hum. Genet., 2001, 92-102, vol. 68.
Kaartinen, V. and Warburton, D., "Fibrillin Controls TGF-β Activation," Nature Genetics, 2003, 331-332, vol. 33.
Neptune, E. et al., "Dyregulation of TGF-β Activation Contributes to Pathogenesis in Marfan Syndrome," Nature Genetics, 2003, 407-411, vol. 33.
Liu, X. et al., "Type III Collagen is Crucial for Collagen I Fibrillogenesis and for Normal Cardiovascular Development," Proc. Natl. Acad. Sci. USA, 1997, 1852-1856, vol. 94.
Haider, A. et al., "Increased Left Ventricular Mass and Hypertrophy are Associated with Increased Risk for Sudden Death," JACC, 1998, 1454-1459, vol. 32, No. 5.
Harjai, K., "Potential New Cardiovascular Risk Factors: Left Ventricular Hypertrophy, Homocysteine, Lipoprotein(a), . . . " Ann. Intern. Med., 1999, 376-386, vol. 131.
Verdecchia, P. et al., "Left Ventricular Mass and Cardiovascular Morbidity in Essential Hypertension: The MAVI Study," J. Amer. Col. Cardio., 2001, 1829-1835, vol. 38, No. 7.

(Continued)

*Primary Examiner*—Thaian N. Ton
*Assistant Examiner*—Marcia S Noble
(74) *Attorney, Agent, or Firm*—Robert D. Katz, Esq.; Cooper & Dunham LLP

(57) ABSTRACT

This invention relates to the production of dual models of Congenital Heart Defects and Hypertrophic Cardiomyopathy with the use of mice which are genetically modified by transgenic (gene-knockout) techniques. The present invention produces knockout mice that show multiple cardiovascular malformations which will serve as a model of cardiovascular diseases for the screening of potential drugs against ventricular remodeling, malignant arrhythmias, primary pulmonary hypertension, and degenerative valvular diseases, and congenital heart disease.

7 Claims, 11 Drawing Sheets

OTHER PUBLICATIONS

Runo, J. and Lloyd, J., "Primary Pulmonary Hypertension," The Lancet, 2003, 1533-1544, vol. 361.

Deng, Z. et al., "Familial Primary Pulmonary Hypertension (Gene PPH1) is Caused by Mutations . . . ," Am. J. Hum. Genet., 2000, 737-744, vol. 67.

Humbert, M. et al., "BMPR2 Germline Mutations in Pulmonary Hypertension Associated with Fenfluramine Derivatives," Eur. Respir. J., 2002, 518-523, vol. 20.

Harrison, R. et al., "Molecular and Functional Analysis Identifies ALK-1 as the Predominant Cause of Pulmonary . . . ," J. Med. Genetics, 2003, 865-871, vol. 40, No. 12.

West, J. et al., "Pulmonary Hypertension in Transgenic Mice Expressing a Dominant-Negative BMPRII Gene in Smooth Muscle," Circulation Research, 2004, 1-7, vol. 94.

Zhang, S. et al., "Bone Morphogenetic Proteins Induce Apoptosis in Human Pulmonary . . . ," Am. J. Physiol. Lung Cell Mol. Physiol., 2003, L740-L754, vol. 285.

Morrell, N. et al., "Altered Growth Responses of Pulmonary Artery Smooth Muscle Cells From Patients with Primary Pulmonary . . . ," Circulation, 2001, 790-795, vol. 104.

Champion, H. et al., "Adenoviral Gene Transfer of Endothelial Nitric-Oxide Synthase (eNOS) Partially Restores . . . ," PNAS, 2002, 13248-13253, vol. 99, No. 20.

Cluzeaut, F. and Maurer-Schultze, B., "Proliferation of Cardiomyocytes and Interstitial Cells in the Cardiac Muscle . . . ," Cell Tissue Kinet., 1986, 267-274, vol. 19.

Leu, M. et al., "Characterisation of Postnatal Growth of the Murine Heart," Anat. Embryol., 2001, 217-224, vol. 204.

Delot, E. et al., "BMP Signaling is Required for Septation of the Outflow Tract of the Mammalian Heart," Development, 2003, 209-220, vol. 130.

Brown, C. et al., "The Cardiac Determination Factor, Nkx2-5, Is Activated by Mutual Cofactors . . . ," The Journal of Biochemistry, 2004, 10659-10669, vol. 279, No. 11.

Donoso, L. et al., "Clinical Variability of Stickler Syndrome: Role of Exon 2 of the Collagen COL2A1 Gene," Survey of Ophthalmology, 2003, 191-203, vol. 48, No. 2.

Donoso, L. et al., "Identification of a Stop Codon Mutation in Exon 2 of the Collagen 2A1 Gene . . . ," American Journal of Ophthalmology, 720-727, vol. 134, No. 5.

Gaio, U. et al., "A Role of the Cryptic Gene in the Correct Establishment of the Left-Right Axis," Current Biology, 1999, 1339-1342, vol. 9.

Gupta, S. et al., "A Frame Shift Mutation in a Tissue-Specific Alternatively Spliced Exon of Collagen 2A1 . . . ," American Journal of Ophthalmology, 2002, 203-210, vol. 133.

Goldmuntz, E. et al., "CFC1 Mutations in Patients with Transposition of the Great Arteries and Double-Outlet Right Ventricle," Am. J. Hum. Genet., 2002, 776-780, vol. 70.

Ito, M. et al., "Involvement of the TRAP220 Component of the TRAP/SMCC Coactivator Complex in Embryonic . . . ," Molecular Cell, 2000, 683-693, vol. 5.

Molkentin, J. et al., "Direct Activation of a GATA6 Cardiac Enhancer by Nkx2.5: Evidence for Reinforcing Regulatory . . . ," Developmental Biology, 2000, 301-309, vol. 317.

Muncke, N. et al., "Missense Mutations and Gene Interruption in PROSIT240, a Novel TRAP240-Like Gene, in Patients . . . ," Circulation, 2003, 2843-2850, vol. 108.

Patient, R. and McGhee, J., "The GATA Family (Vertebrates and Intervertebrates)," Current Opinion in Genetics & Development, 2002, 416-422, vol. 12.

Peterkin, T. et al., "The Role of GATA-4, -5, and -6 in Vertebrate Heart Development," Cell & Developmental Biology, 2005, 83-94, vol. 16.

Richards, A. et al., "COL2A1 Exon 2 Mutations: Relevance to the Stickler and Wagner Syndromes," British Journal of Ophthalmology, 2000, 364-371, vol. 84.

Van Der Hout, A. et al., "Occurrence of Deletion of a COL2A1 Allele as th Mutation in Stickler Syndrome Shows that . . . ," Human Mutation, 2002, 1-4, Mutation in Brief #532.

Persson, U. et al., "The L45 Loop in Type I Receptors for TGF-Beta Family Members is a Critical Determinant in Specifying . . . ," FEBS Letters, 1998, 83-87, vol. 434.

Rosendahl, A. et al., "Activation of Bone Morphogenetic Protein/Smad Signaling in Bronchial Epithelial Cells . . . ," Am. J. Respir. Cell. Mol. Biol., 2002, 160-169, vol. 27.

Chuva De Sousa Lopes, S.M. et al., "Connective Tissue Growth Factor Expression and Smad Signaling During Mouse Heart . . . ," Developmental Dynamics, 2004, 542-550, vol. 231.

Medugorac, I., "Myocardial Collagen in Different Forms of Heart Hypertrophy in the Rat," Research in Experimental Medicine, 1980, 201-211, vol. 177.

Taussig, H. and Bing, R., "Complete Transposition of the Aorta and a Levoposition of the Pulmonary Artery," American Heart Journal, 1949, 551-559.

Cheah, K. et al., "The Mouse Col2a-1 Gene is Highly Conserved and is Linked to Int-1 on Chromosome 15," Mammalian Genome, 1991, 171-183.

Wood, A. et al., "The Transient Expressiong of Type II Collagen at Tissue Interfaces During Mammalian Craniofacial Development," Development, 1991, 955-968, vol. 111.

Virmani, R. et al., "Sudden Cardiac Death," Cardiovascular Pathology, 2001, 211-218, vol. 10.

Honda, M. et al., "Biochemical and Structural Remodeling of Collagen in the Right Ventricular . . . ," Japanese Circualation Journal, 1992, 392-402, vol. 56.

Gardi, C. et al., "Cardiac Collagen Changes during the Development of Right Ventricular . . . ," Experimental and Molecular Pathology, 1994, 100-107, vol. 60.

Izumi, M. et al., "Bone Morphogenetic Protein-2 Inhibits Serum Deprivation-induced Apoptosis . . . ," The Journal of Biological Chemistry, 2001, 31133-41, vol. 276, No. 33.

Weber, K. et al., "Collagen Network of the Myocardium: Function, Structural Remodeling and Regulatory Mechanisms," J. Mol. Cell Cardiol., 1994, 279-292, vol. 26.

Yoshikane, H. et al., "Collagen in Dilated Cariomyopathy," Japanese Circulation Journal, 1992, 899-910, vol. 56.

Monzen, K. et al., "A Role for Bone Morphogenetic Protein Signaling in Cardiomyocyte Differenciation," Trends Cardiovasc. Med., 2002, 263-269, vol. 12, No. 6.

Belmont, J. et al., "Molecular Genetics of Heterotaxy Syndromes," Current Opinion in Cardiology, 2004, 216-220, vol. 19.

Diglio, M. et al., "Complete Transposition of the Great Arteries: Patterns of Congenital Heart Disease . . . ," Circulation, 2001, 2809-2814, vol. 104.

Parlakian, A. et al., "Targeted Inactivation of Serum Response Factor in the Developing Heart Results . . . ," Molecular and Cellular Biology, 2004, 5281-5289.

Purandare, S. et al., "Development and Disease: A Complex Syndrome of Left-Right Axis . . . ," Development, 2002, 2293-2302, vol. 129.

* cited by examiner

Figure 1. Pedigree of 191-IIA-/- mice
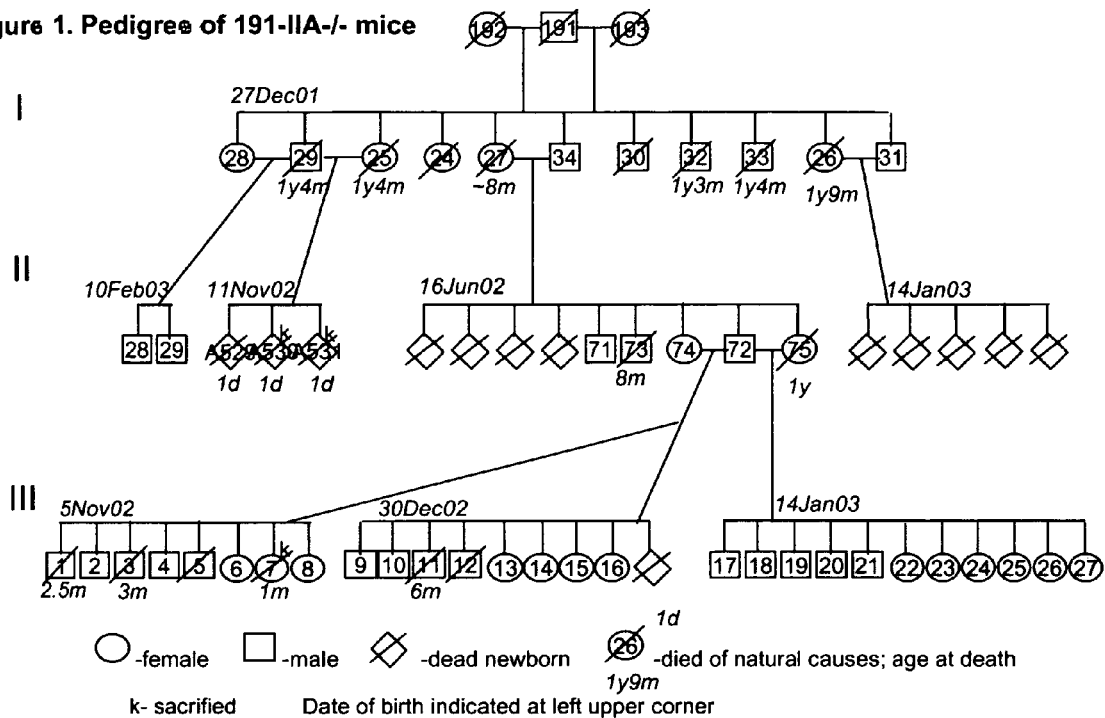
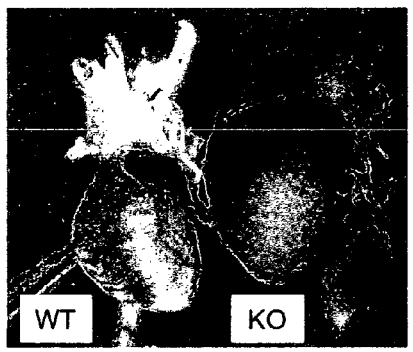
191.3 male (3 months)
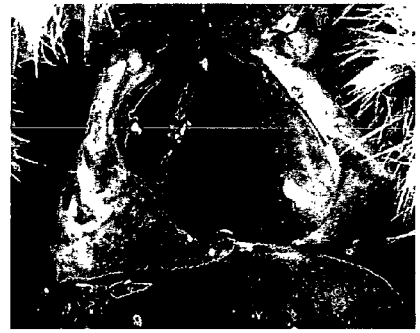
191.11 male (6 months)
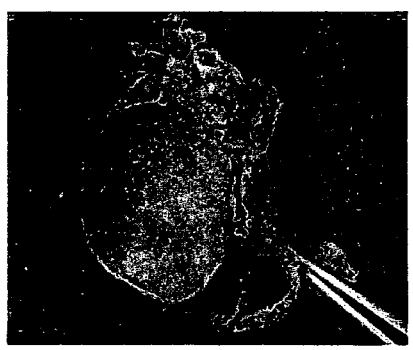
191.73 male (9 months)
191.75 male (12 months)

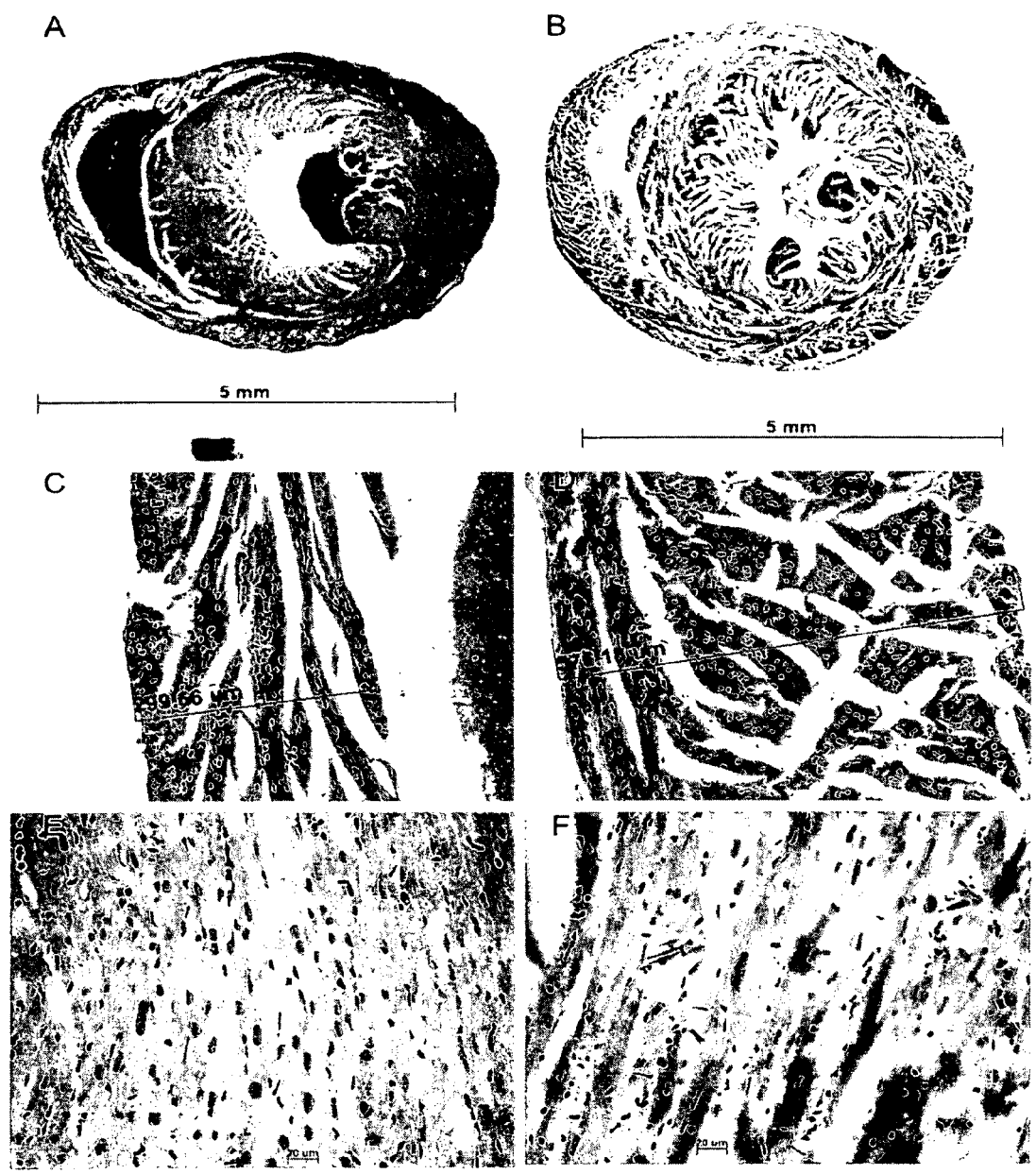
Figure 2. H&E stainings of 191.1 heart

Figure 3. H&E stainings of 191.3 heart
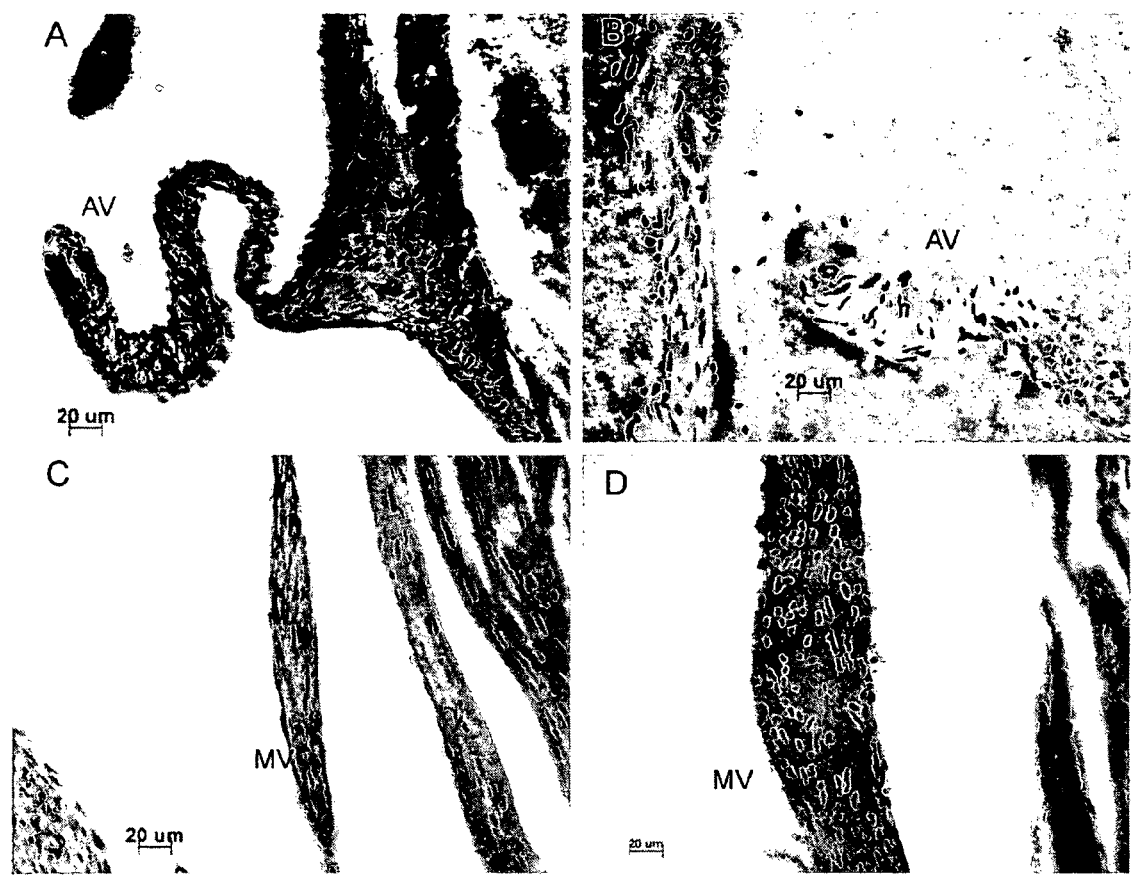

Figure 4. H&E stainings of older 191-IIA-/- mice
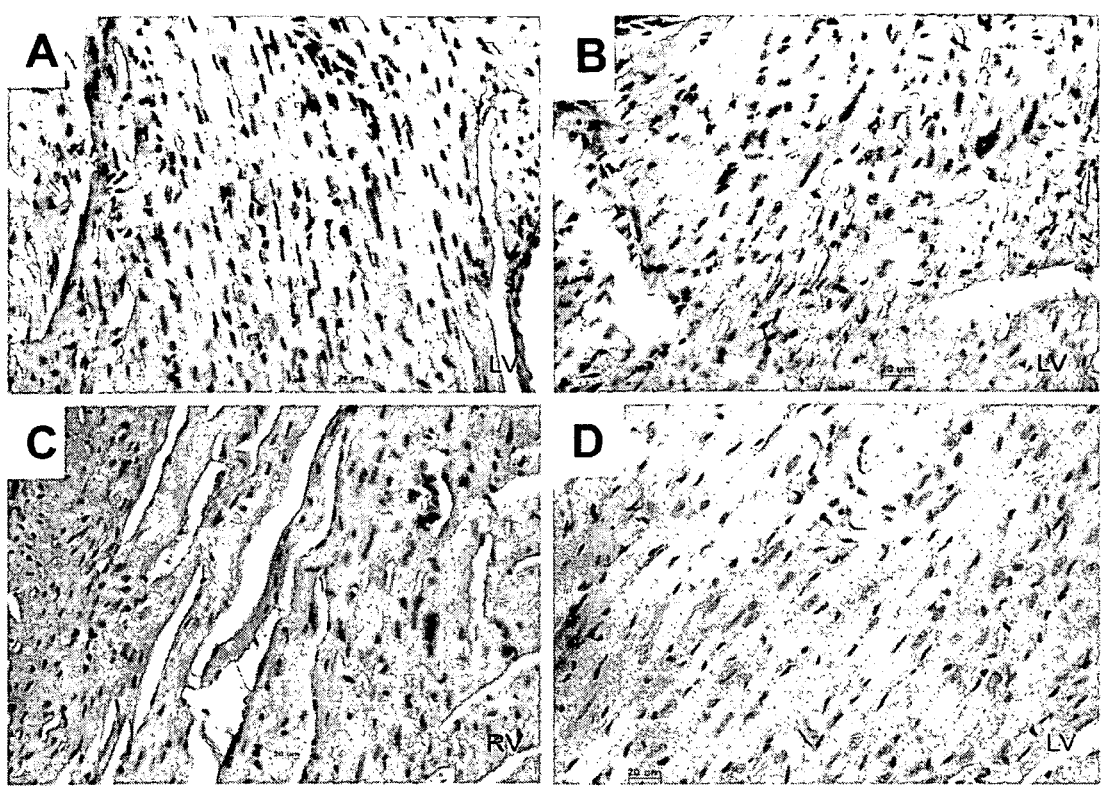

Figure 5. Normal expression pattern of IIA mRNA and generation of IIA-/- mice
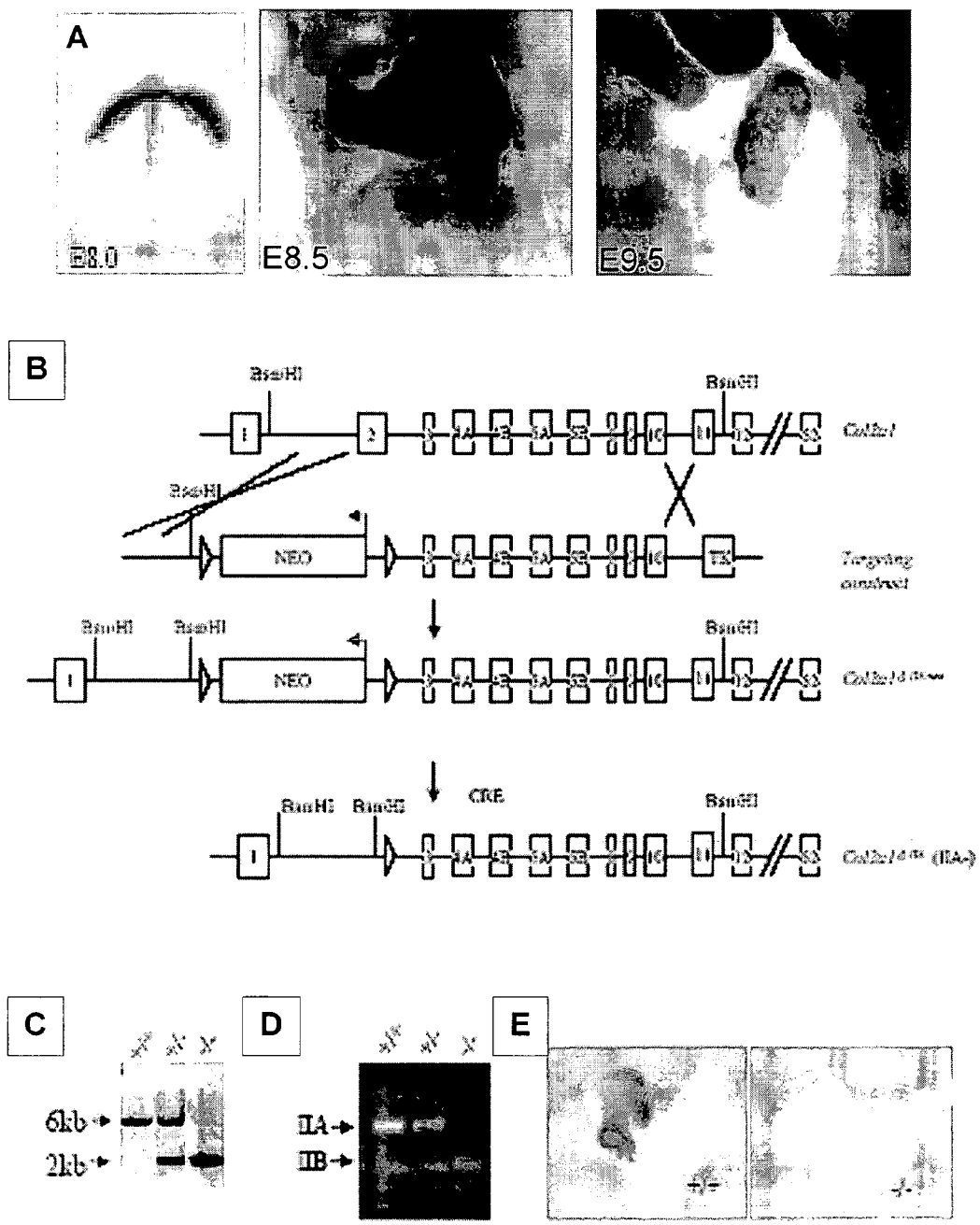

Figure 6. Cardiovascular Defects in Newborn CoIIA-/- Mutants
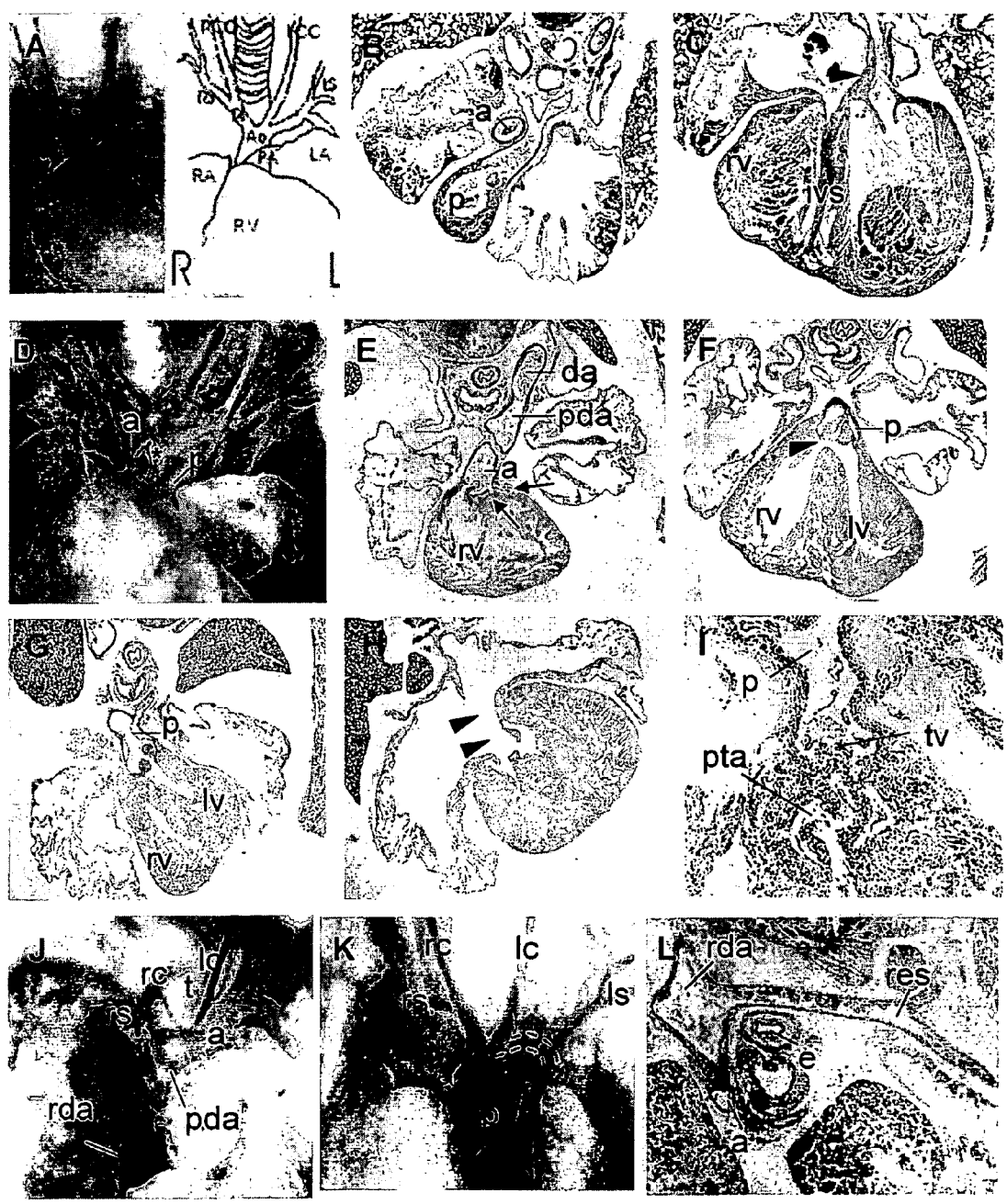

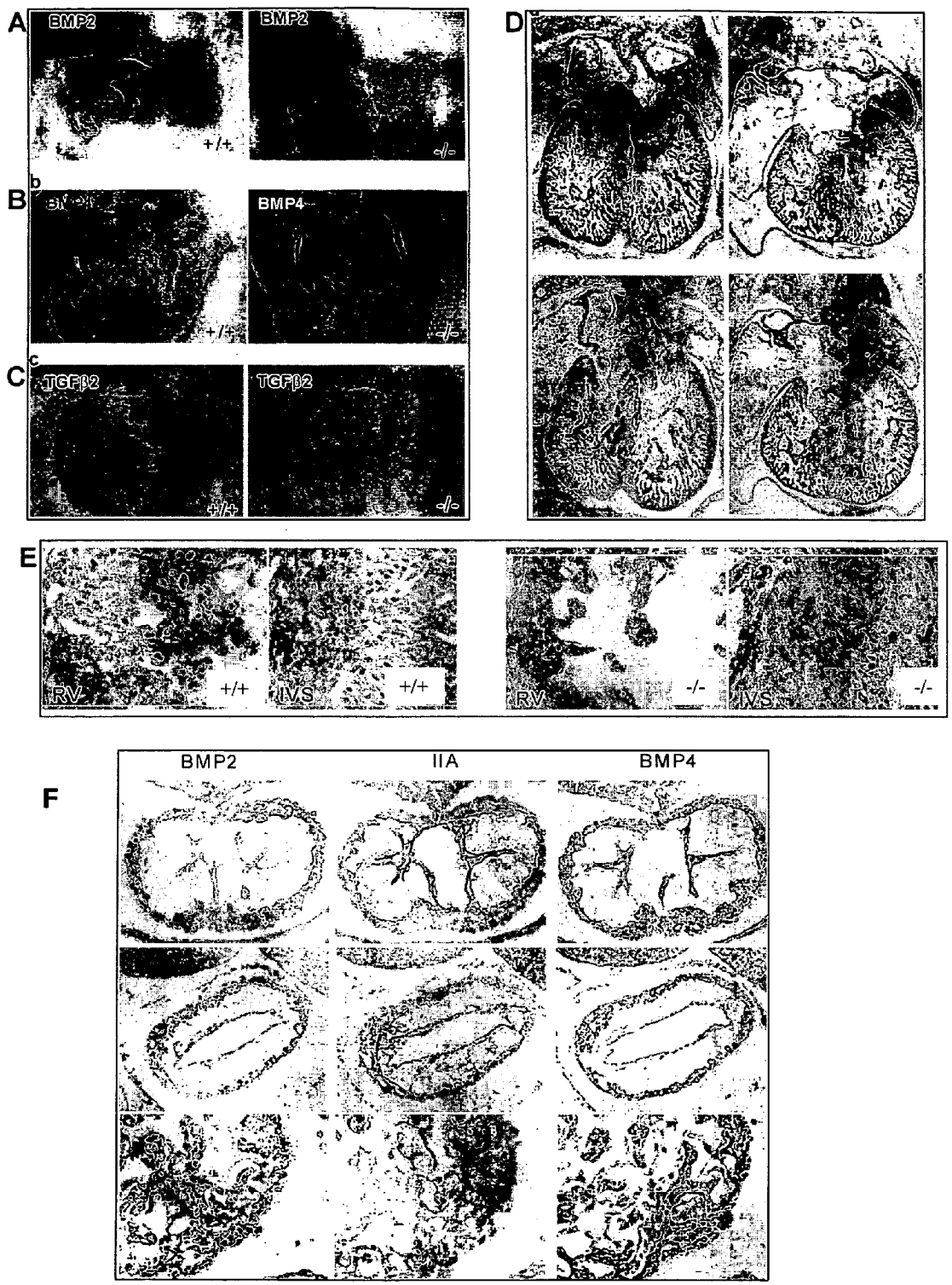
Figure 7. Defective BMP signaling in IIA-/- embryos

Figure 8. Type IIA - *Nkx2.5* cross-dependant regulatory loop
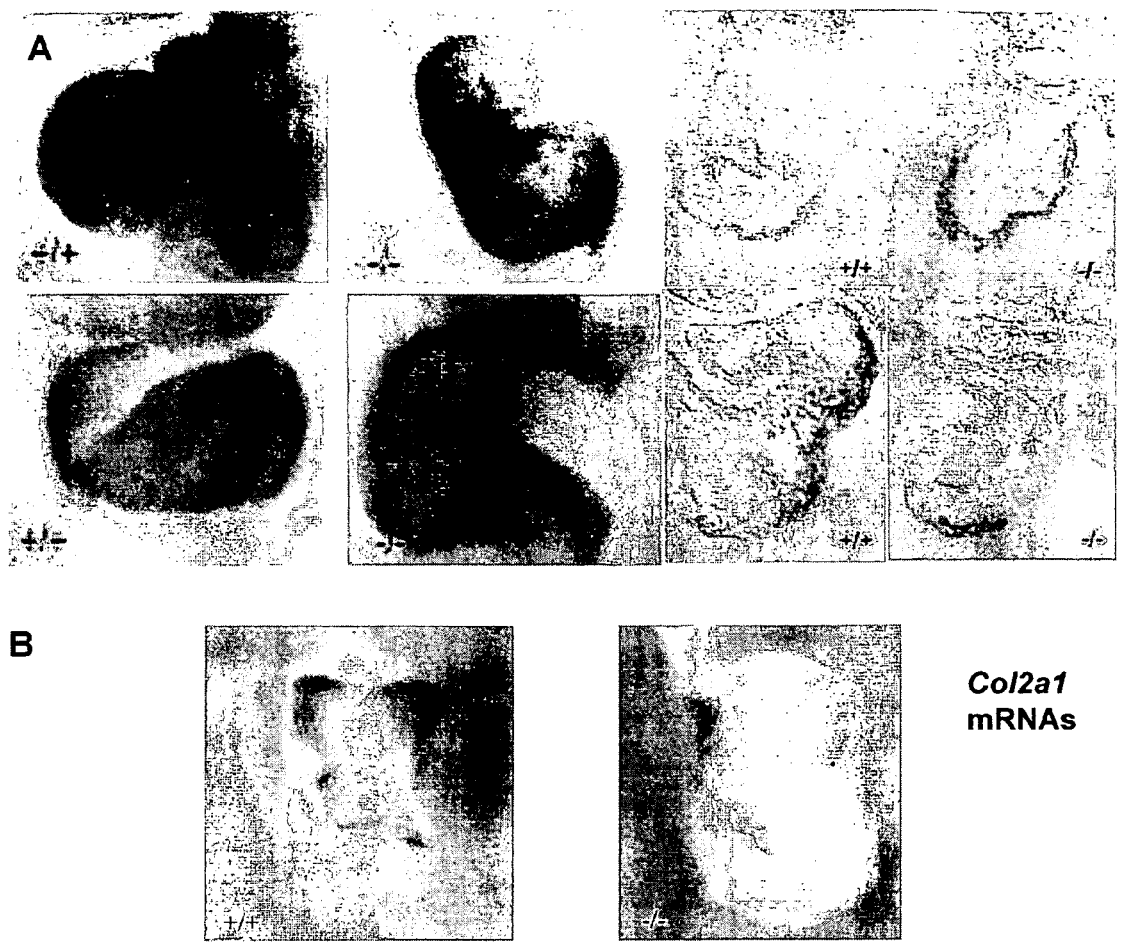
*Col2a1* mRNAs

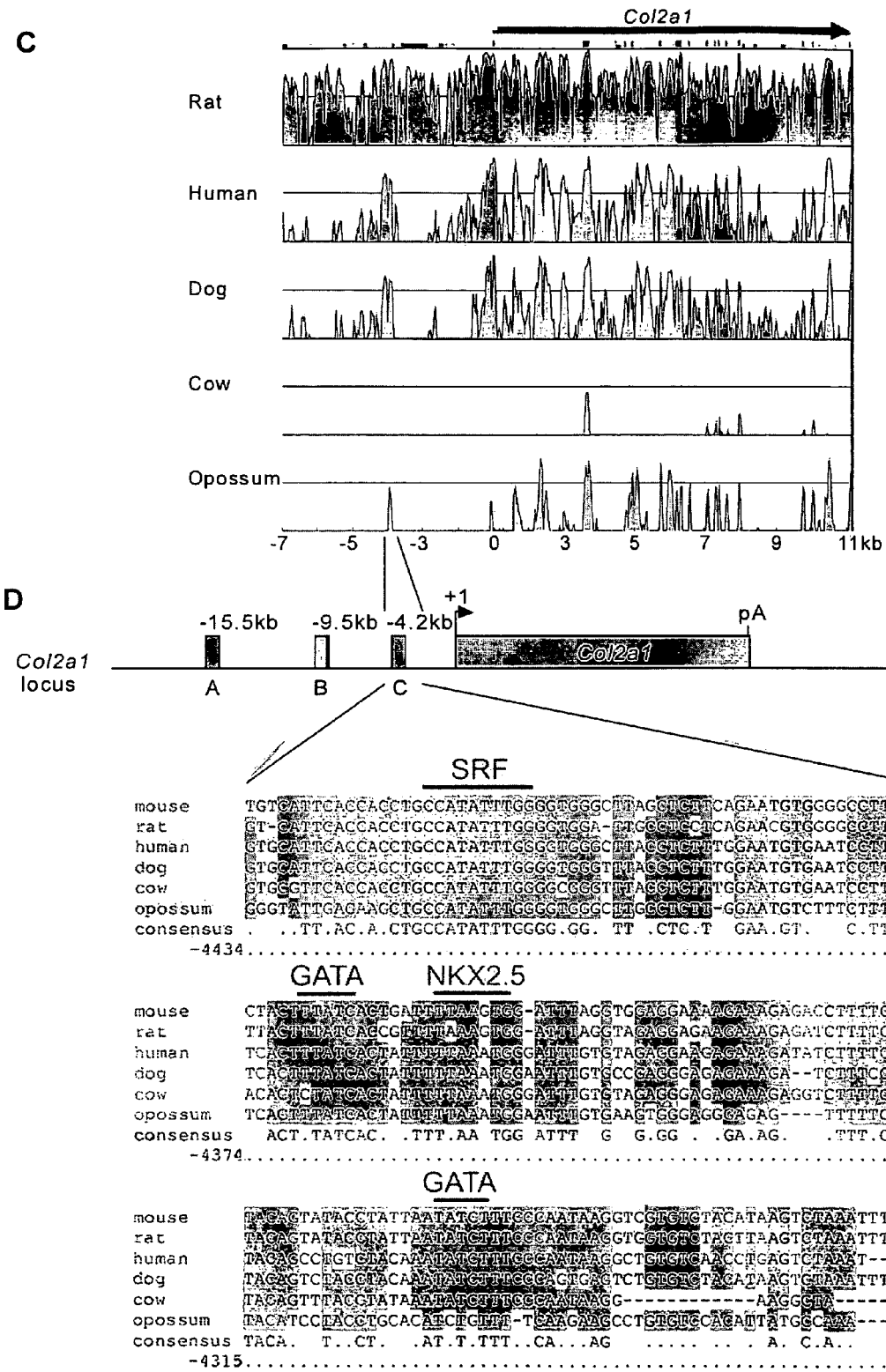
Figure 8. Type IIA - *Nkx2.5* cross-dependant regulatory loop cont'd

Figure 8. Type IIA - *Nkx2.5* cross-dependant regulatory loop cont'd
E
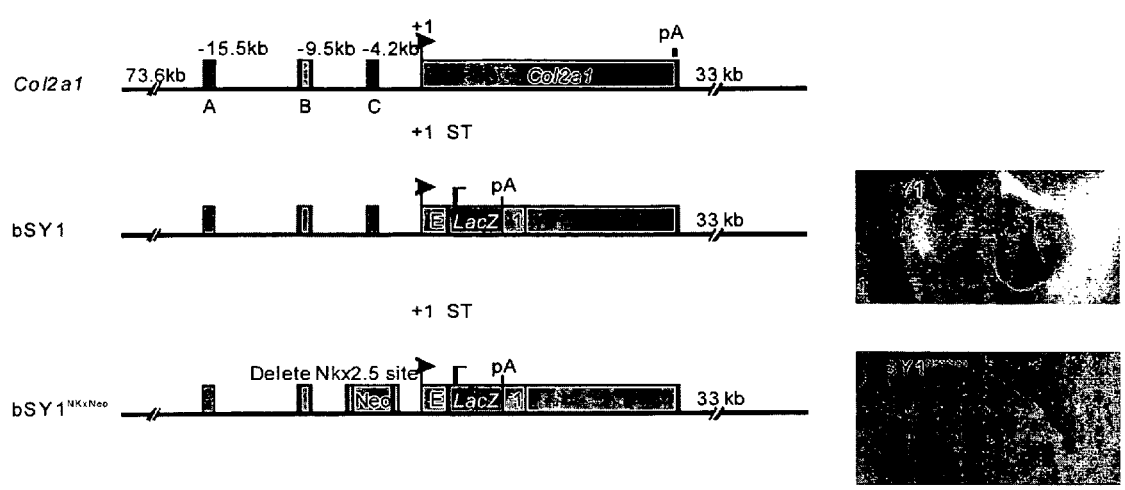

Figure 9. Summary of roles of IIA procollagen in *Nkx2.5* regulatory loop during cardiovascular morphogenesis
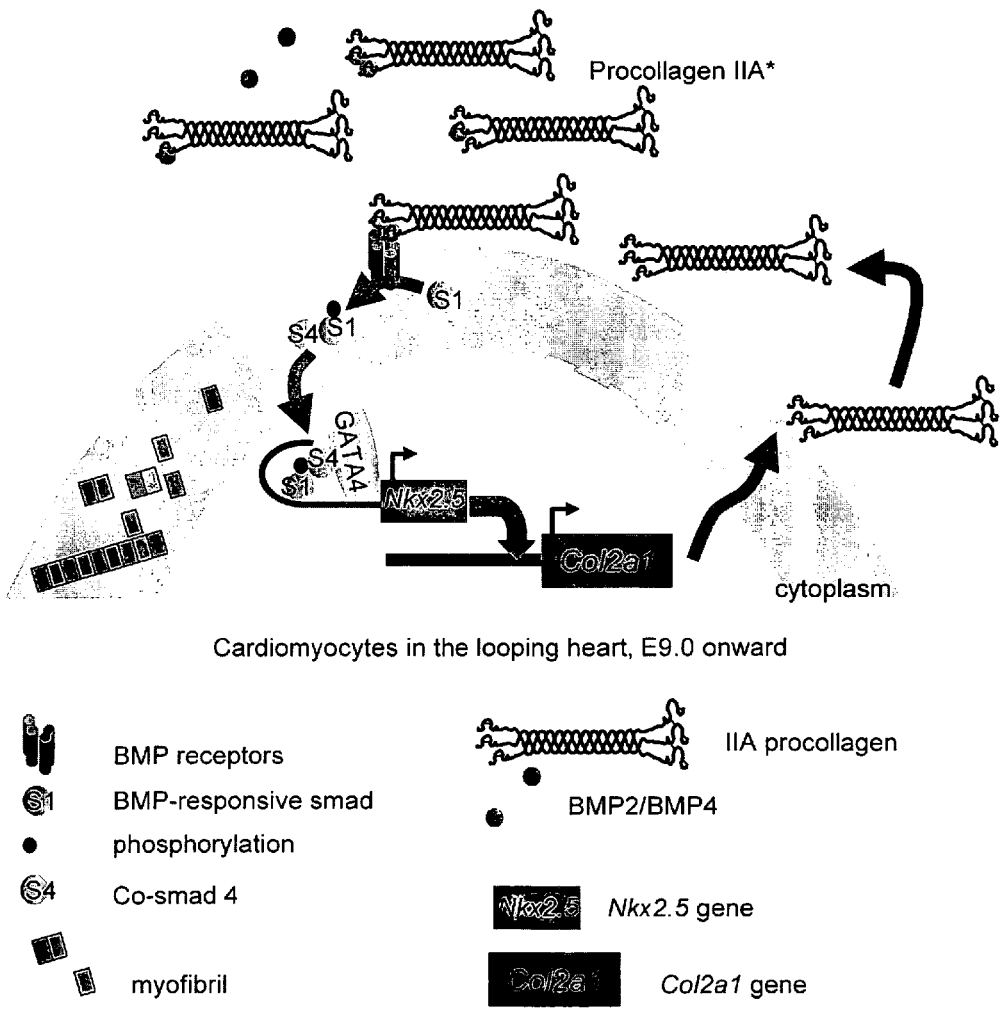

SEQUENCE LISTING

```
<160> NUMBER OF SEQ ID NOS: 18

<210> SEQ ID NO 1
<211> LENGTH: 60
<212> TYPE: DNA
<213> ORGANISM: mouse

<400> SEQUENCE: 1
tgtcattcac cacctgccat atttggggtg ggcttagctc ttcagaatgt ggggccttcc    60

<210> SEQ ID NO 2
<211> LENGTH: 58
<212> TYPE: DNA
<213> ORGANISM: rat

<400> SEQUENCE: 2
gtcattcacc acctgccata tttggggtgg attgcctcct cagaacgtgg ggccttcc      58

<210> SEQ ID NO 3
<211> LENGTH: 60
```

```
<212> TYPE: DNA
<213> ORGANISM: human

<400> SEQUENCE: 3
gtgcattcac cacctgccat atttggggtg ggcttacctc tttggaatgt gaatccttct        60

<210> SEQ ID NO 4
<211> LENGTH: 60
<212> TYPE: DNA
<213> ORGANISM: dog

<400> SEQUENCE: 4
gtgcattcac cacctgccat atttggggtg ggtttacctc tttggaatgt gaatccttcc        60

<210> SEQ ID NO 5
<211> LENGTH: 60
<212> TYPE: DNA
<213> ORGANISM: cow

<400> SEQUENCE: 5
gtgcgttcac cacctgccat atttggggcg ggtttacctc tttggaatgt gaatccttcc        60

<210> SEQ ID NO 6
<211> LENGTH: 59
<212> TYPE: DNA
<213> ORGANISM: opossum

<400> SEQUENCE: 6
gggtattgac aagctgccat atttggggtg ggcttgcctc ttggaatgtc tttctttcc         59

<210> SEQ ID NO 7
<211> LENGTH: 59
<212> TYPE: DNA
<213> ORGANISM: mouse

<400> SEQUENCE: 7
ctactttatc actgatttta agtggattta ggtggaggaa aagaaagaga cctttctctt        59

<210> SEQ ID NO 8
<211> LENGTH: 59
<212> TYPE: DNA
<213> ORGANISM: rat

<400> SEQUENCE: 8
ttactttatc accgttttaa agtggattta ggtagaggag aagaaagaga tcttttctt        59

<210> SEQ ID NO 9
<211> LENGTH: 60
<212> TYPE: DNA
<213> ORGANISM: human

<400> SEQUENCE: 9
tcactttatc actattttta aatgggattt gtgtagagga agagaaagat atcttttctt        60

<210> SEQ ID NO 10
<211> LENGTH: 58
<212> TYPE: DNA
<213> ORGANISM: dog

<400> SEQUENCE: 10
tcactttatc actattttta aatggaattt gtgccgaggg agagaaagat ctttcctt          58

<210> SEQ ID NO 11
```

```
<211> LENGTH: 60
<212> TYPE: DNA
<213> ORGANISM: cow

<400> SEQUENCE: 11
acactctatc actatttta aatgggattt gtgtagaggg agagaaagag gtcttttctt      60

<210> SEQ ID NO 12
<211> LENGTH: 56
<212> TYPE: DNA
<213> ORGANISM: opossum

<400> SEQUENCE: 12
tcactttatc actatttta aatggaattt gtgaagtggg agggagagtt tttctt          56

<210> SEQ ID NO 13
<211> LENGTH: 58
<212> TYPE: DNA
<213> ORGANISM: mouse

<400> SEQUENCE: 13
tacagtatac ctattaatat ctttcccaat aaggtcgtgt ctacataagt ctaaattt       58

<210> SEQ ID NO 14
<211> LENGTH: 58
<212> TYPE: DNA
<213> ORGANISM: rat

<400> SEQUENCE: 14
tacagtatac ctattaatat ctttcccaat aaggtggtgt ctacttaagt ctaaattt       58

<210> SEQ ID NO 15
<211> LENGTH: 56
<212> TYPE: DNA
<213> ORGANISM: human

<400> SEQUENCE: 15
tacagcctgt ctacaaatat ctttcccaat aaggctgtgt caacctgagt ctaaat         56

<210> SEQ ID NO 16
<211> LENGTH: 58
<212> TYPE: DNA
<213> ORGANISM: dog

<400> SEQUENCE: 16
tacagtctac ctacaaatat ctttcccagt gagtctgtgt ctacataagt ctaaattt       58

<210> SEQ ID NO 17
<211> LENGTH: 41
<212> TYPE: DNA
<213> ORGANISM: cow

<400> SEQUENCE: 17
tacagtttac ctataaatat ctttcccaat aaggaaggct a                         41

<210> SEQ ID NO 18
<211> LENGTH: 54
<212> TYPE: DNA
<213> ORGANISM: opossum

<400> SEQUENCE: 18
tacatcctac ctgcacatct gttttcaaga agcctgtgtc cacattatgc caaa           54
```

MUTANT MICE COMPRISING A MUTATED TYPE II PROCOLLAGEN ALPHA-1

This application claims priority of U.S. Provisional Application No. 60/591,935, filed Jul. 26, 2004, the contents of which are hereby incorporated by reference into this application.

Throughout this application, various publications are referenced. Full citations for these publications may be found immediately preceding the claims. The disclosures of these publications are hereby incorporated by reference into this application in order to more fully describe the state of the art as of the date of the invention described and claimed herein.

BACKGROUND OF THE INVENTION

Sudden cardiac death (SCD) is a major public health problem responsible for up to 63% of cardiac deaths among persons older than 35 in the United States.[1] While acute ischemic heart disease is the major cause of SCD in this population, one of the most common causes of sudden death in adolescents and young adults less than 40 years old is hypertrophic cardiomyopathy (HCM). Other less frequent causes include anomalous coronary arteries, Marfan's syndrome, arrhythmogenic right ventricular dysplasia, myocarditis, aortic valvular stenosis and coronary atherosclerotic disease. HCM is an inherited disease of cardiac muscles where there is asymmetric or symmetric left ventricular hypertrophy with a non-dilated, hyperdynamic chamber in the absence of secondary causes. It affects men and women equally and is characterized by highly variable clinical courses, heterogeneous pathology and complex genetic expression. Depending on underlying mutations, HCM can be compatible with normal longevity at one end of disease spectrum, but at the other end, it is the most common cause of SCD in young athletes. The causes of SCD are assumed to be complex ventricular tachycardia or fibrillation originating on an electrically unstable myocardial substrate, but bradycardias and severe obstruction are also suggested. Prevention of SCD in HCM continues to be a major challenge for clinicians. The use of implantable cardioverter defibrillator (ICD) in tertiary centers has been reported to be useful, but the patients may still suffer from end-stage heart failure and atrial fibrillation with attendant risk of thromboembolic strokes.[3,4] A pathological model of HCM will be critical to understand the development of HCM and causes of SCD, and that will be important for prevention and treatment. Currently, the known disease genes account for about 50-70% of all cases of familial hypertrophic cardiomyopathy.[5] Most of the primary cardiomyopathies in humans, hypertrophic or dilated, are due to mutations in contractile proteins, cytoskeletal proteins, or gap junction proteins, and are in most cases the direct consequences of structural defects.

The cardiac extracellular matrix plays multiple important functional roles as the substrate for cell adhesions and scaffolding, as the signals for cell survival, as a reservoir for growth factors, and as the major determinant of tissue mechanics. Collagen is a major component of extracellular matrix in the mammalian hearts and exhibits a dynamic expression pattern and isoform diversity during development and in pathological conditions.[5] In the adult myocardium, type I collagen comprises 80% of total collagen and together with type III collagen forms a network of fibrillar collagen that supports individual cardiomyocytes and smooth muscle cells, and organizes muscle bundles, conduction system, and coronary vasculature into cohesive contractile units. In contrast, type III collagen is the major component in neonatal rat hearts, comprising about one-third of the total collagen content, and thus the visco-elasticity is different from that of adult myocardium. In rodent models of right ventricular hypertrophy, the ratio of types I and III collagen is clearly altered.[9, 10] Types II and VIII collagen are transiently expressed during cardiac development and have been implicated in cardiac morphogenesis. Although type II collagen was classically thought to be cartilage specific, a much wider tissue distribution has been shown during mouse embryogenesis. The mouse α1(II) collagen gene (Col2a-1) is transiently expressed in many non-cartilaginous tissues such as the notochord, neural retina, tail tendon, heart, surface ectoderm, calvarial mesenchyme, fetal brain, the sensory epithelium of the inner ear and the apical ectodermal ridge of the forming limb buds (AER). Alternative splicing of exon 2 produces type II procollagen mRNAs that either include (IIA mRNA) or exclude (IIB mRNA) this exon. Type IIA mRNA is abundant in cells of the epimyocardium in both the atria and ventricles of 9.5-day embryos but rapidly diminishes by 10.5 days. After 12.5 days, IIB mRNA levels increase rapidly and finally exceed IIA mRNAs. By 16.5 days, IIB mRNAs are the major Col2a-1 transcripts, predominantly expressed in maturing chondrocytes.[13] Postmortem analyses from one hospital revealed that defects in cardiac septation were present in 2 infants with hypochondrogenesis, a disorder of type II collagen.

How type IIA collagen contributes to cardiac morphogenesis is not yet clearly defined, but recent studies suggest that it may modulate growth factors. Of note, exon2 of the type II collagen gene (Col2a-1), which is included in IIA mRNA, encodes a cysteine-rich globular domain in the amino-propeptide of pro-α1(II) collagen chains. This cysteine-rich domain has been shown to bind bone morphogenic proteins (eg. BMP2) and Transforming Growth Factor (TGF)-β1 in in vitro assays.

TGF-β1 and BMP-2 belong to the transforming growth factor-β superfamily that regulates growth and differentiation. Like other members of the TGF-β superfamily (TGF-β/Activin/Nodal and BMP/GDF/MIS subfamilies), their diverse biological effects are mediated by the formation of heteromeric complexes of type I and type II serine/threonine kinase receptors, phosphorylation of the type I receptor by type II receptor and subsequent activation of Smad proteins. Receptor-activated Smads (R-Smads, Smads 1-3, 5, 8) are phosphorylated by type I receptor kinases, form heteromeric complexes with the common mediator Smads (co-Smads, Smad4) and translocate into the nucleus where they interact with specific transcription factors and co-regulators to modulate gene expression. R-Smads2 and 3 respond to the TGF-β subfamily, while R-Smads I, 5, and 8 primarily to the BMP subfamily. Two inhibitory Smads (I-Smad), Smad6 and Smad7, negatively regulate TGF-β/BMP signaling by competing with Smad4 for the binding of activated R-Smads, inhibiting phosphorylation of R-Smads, or targeting the receptors for degradation.[16, 17] Both TGF-β1 and BMP-2 play crucial roles in various aspects of heart development, especially in cardiomyocyte differentiation, valvulogenesis, and outflow tract and septal development.[18-21] TGF-β1 exerts diverse biological activities in postnatal hearts. It controls the expression of major histocompatibility complex, induces production of the extracellular matrix proteins by cardiac fibroblasts, regulates vascular smooth muscle cell phenotype, induces cardiac hypertrophy, and enhances β-adrenergic signaling. There is limited information about the role of BMP-2 in postnatal mammalian hearts. In rat neonatal cardiomyocyte culture, BMP-2 exerts anti-apoptotic effect by activation of the Smad1 pathway and enhances contractility by activation of phosphatidylinositol 3 kinase pathway.[22, 23] Clinically, primary pulmonary hypertension, a disorder of increased proliferation of endothelial and smooth muscle cells in pulmonary arteries, has been linked to mutations in type II receptors for BMP (BMPR-II).[24,25]

Recent studies in the murine model of Marfan syndrome also highlight the active role of extracellular matrix, in this instance, fibrillin, in modulating TGF-β signaling.[26,27]

In human dilated cardiomyopathy, increased perimysial fibrosis is associated with increase in types I, III, and VI collagen content, and type V collagen is increased in intracellular matrix of myocardium. Type II collagen is not expressed in normal hearts or dilated cardiomyopathy.[28] Whether or not type II collagen is ectopically expressed in hypertrophic cardiomyopathy in humans remains to be investigated. A variety of mouse models of cardiomyopathies and altered contractility focus on targeted mutations of aforementioned proteins, cell cycle regulatory proteins, regulator proteins involved in calcium metabolisms, and subunits of the adrenergic receptor signal transduction cascade. The concept of extracellular matrix modulating tissue patterning and cardiomyocyte differentiation is not novel although matrix defects have not generally been considered as possible source of cardiomyopathies. Even in the mouse with targeted deletion of type III collagen, there was no cardiac abnormality and sudden death was due to rupture of the aorta.[29] The adult 191-IIA mutant mice described in this application are therefore a very important model for cardiomyopathy-induced death which may occur suddenly.

Taussig-Bing Anomaly (TBA) is a rare but complex congenital heart disease and comprises of a double outlet right ventricle (DORV) with subpulmonary ventricular septal defect (VSD). Aortic and pulmonary trunks are transposed. Next to Tetralogy of Fallot, TBA is the most common variant of DORV. Infants with TBA often present with congestive heart failure and pulmonary hypertension. Its management is complicated by associated vascular defects such as coronary anomalies, subaortic stenosis, aortic arch coarctation or interruption. Currently recommended treatment is complete correction in a single operation, typically involving arterial switch operation, VSD repair, corrective repair of aortic obstruction, and translocation of anomalous coronary arteries. Therefore, detailed mapping of these vascular defects is crucial to the success of corrective surgery. TOGA is the most frequently diagnosed complex cyanotic heart defects in newborns (ref) and involves ventriculoarterial discordance. Genetics of human TBA or TOGA has focused on candidate genes involved in left-right asymmetry or heterotaxy syndrome. Mutations in three human genes have been associated with TOGA: Zinc-finger transcription factor ZIC3 {Digilio, M. C. et al. Complete transposition of the great arteries: patterns of congenital heart disease in familial precurrence. *Circulation* 104, 2809-14 (2001).} {Belmont, J. W., Mohapatra, B., Towbin, J. A. & Ware, S. M. Molecular genetics of heterotaxy syndromes. *Curr Opin Cardiol* 19, 216-20 (2004).}, CFC1 (human CRYPTIC gene) {Goldmuntz, E. et al. CFC1 mutations in patients with transposition of the great arteries and double-outlet right ventricle. *Am J Hum Genet* 70, 776-80 (2002).}, and PROSIT240 {Muncke, N. et al. Missense mutations and gene interruption in PROSIT240, a novel TRAP240-like gene, in patients with congenital heart defect (transposition of the great arteries). *Circulation* 108, 2843-50 (2003).}. These clinical findings have been validated in mouse models of genetic ablation of Zic3 {Purandare, S. M. et al. A complex syndrome of left-right axis, central nervous system and axial skeleton defects in Zic3 mutant mice. *Development* 129, 2293-302 (2002).}, cryptic (EGF-CFC) {Gaio, U. et al. A role of the cryptic gene in the correct establishment of the left-right axis. *Curr Biol* 9, 1339-42 (1999).}, and TRAP220 {Ito, M., Yuan, C. X., Okano, H. J., Darnell, R. B. & Roeder, R. G. Involvement of the TRAP220 component of the TRAP/SMCC coactivator complex in embryonic development and thyroid hormone action. *Mol Cell* 5, 683-93 (2000).}.

Here we describe that mice carrying the IIA mutation on a C57/BL6 genetic background is a novel mouse model of TBA and TOGA. Mutations in the human COL2A1 gene are dominant, resulting in chondrodysplasias with a spectrum of severity from prenatal lethality to mild deformity. Dominant mutations in exon2 have been found in the Stickler Syndrome and Wagner's Syndromes which are also associated with eye defects {Richards, A. J. et al. COL2A1 exon 2 mutations: relevance to the Stickler and Wagner syndromes. *Br J Ophthalmol* 84, 364-71 (2000).} {Van Der Hout, A. H. et al. Occurrence of deletion of a COL2A1 allele as the mutation in Stickler syndrome shows that a collagen type II dosage effect underlies this syndrome. *Hum Mutat* 20, 236 (2002).} {Donoso, L. A. et al. Identification of a stop codon mutation in exon 2 of the collagen 2A1 gene in a large stickler syndrome family. *Am J Ophthalmol* 134, 720-7 (2002).} {Donoso, L. A. et al. Clinical variability of Stickler syndrome: role of exon 2 of the collagen COL2A1 gene. *Surv Ophthalmol* 48, 191-203 (2003).} {Gupta, S. K., Leonard, B. C., Damji, K. F. & Bulman, D. E. A frame shift mutation in a tissue-specific alternatively spliced exon of collagen 2A1 in Wagner's vitreoretinal degeneration. *Am J Ophthalmol* 133, 203-10 (2002).}. However, no cyanotic congenital heart defects has been reported or systematically correlated with mutations in the Col2a1 gene. Only one postmortem study from one hospital has reported defects in cardiac septation in 2 infants with hypochondrogenesis, a disorder of type II collagen {Potocki, L., Abuelo, D. N. & Oyer, C. E. Cardiac malformation in two infants with hypochondrogenesis. *Am J Med Genet* 59, 295-9 (1995).}. Given the profound morbidity and mortality of untreated cyanotic congenital heart disease, IIA procollagen may serve as a novel marker for pre-natal screening of complex congenital heart diseases. As a key modulator of BMP-dependent Nkx2.5 expression in cardiac morphogenesis, IIA procollagen may serve as a novel delivery system of growth factors for myocardial regenerative therapy. Understanding the cellular mechanisms of these cardiovascular defects in IIA null mutants will be paramount in formulating a novel strategy to treat or prevent complex cyanotic heart disease.

SUMMARY OF THE INVENTION

The invention provides two lines of genetically engineered mice where the exon 2 of procollagen IIA gene is flanked by loxP sequences and this exon 2 is deleted by mating with mice expressing Cre-recombinase. Deletion of exon 2 results in deletion of IIA transcript. This in turn results in dual manifestation of cardiovascular defects where one lineage being predominantly C57/BL6 genetic background, dies of severe congenital heart disease (IIA−/−) and the other lineage on an outbred genetic background (C57BL6/ICR/129) develops hypertrophic cardiomyopathy characterized by cardiomyocyte hypertrophy, disarray and valvular fibrosis (191-IIA). This invention provides a method of screening for an agent that diminishes hypertrophy, disarray, and fibrosis, as well as cardiovascular patterning defects by administration of the agent to either 191-IIA adult mice or IIA−/− mutant embryos. Such agent may be synthetic or naturally occurring hormones, growth factors, peptides, or genes carried by suitable vectors for gene transfer. This invention also provides primary cell cultures from hearts or aorta and permanent cell lines derived from the knockout mice. Cells from permanent or primary cell cultures from 191-IIA mice are used to screen for agents that ameliorate or abrogate the processes of hypertrophy, hyperplasia, or fibrosis.

BRIEF DESCRIPTION OF THE FIGURES

FIG. 1 Pedigree of 191-11 A mice

The upper panel summarizes the natural history of sudden death in 191-IIA mice. The lower panel shows four examples of cardiomegaly found in these mice at different ages.

FIG. 2 H&E stainings of 191.1 heart

A C E—from a wild type mouse. B D F—from 191.1 male, a homozygous null mutant for CoIIIA that died at 2 months. A B—Two-chamber short-axis view of the hearts from the wild type (A) and the mutant (B). The left ventricle wall of the mutant is less compacted and is hence thicker than that of the wild type. C D—Right ventricle (RV), 100× total magnification. The RV wall thickness is increased in the mutant. E F—Lateral LV wall, 400× total magnifications. While the cardiomyocytes in the wild type are uniform in size and display parallel orientation in the myocardium (E), the mutant myocardium is characterized by cardiomyocyte hypertrophy and disarray (F).

FIG. 3 H&E stainings of 191.3 heart

A C—Aortic valve (AV) and mitral valve (MV) of a wild type mouse, respectively. B D—AV and MV of 191.3 male that died at 3 months. In the mutant, both valves appear fibrotic. All panels are at 400× total magnification. Scale-.bar—20 µm.

FIG. 4 H&E stainings of older 191-IIA mice

A B—Lateral wall of LV from 254.66 male that died at 8 months. Note the hypercellularity. C—RV of 254.66. Note the hypercellularity and cardiomyocyte hypertrophy. D—Lateral wall of LV from 191.29 male that died at 15 months. As compared with FIGS. 2F, 4A, and 4B, cardiomyocytes in this mouse are less disorganized. All panels are at 400× total magnification. Scale bar—20 µm.

FIG. 5 Normal expression pattern of IIA mRNA and generation of IIA−/− mice

A—Asymmetric distribution of IIA mRNA in normal developing hearts. Whole mount in situ hybridization (WISH) of wild type embryos with IIA-specific probe. At 2-somite pair stage (E8.0), IIA mRNA expression was very strong in the cardiac crescent. At 10-somite pair stage (E8.5), the IIA mRNA expression continues to be very strong in the looping primitive heart tube. At the 27-somite pair stage (E9.5), the IIA mRNA expression is the highest in the bulbous cordis and outflow tract, followed by the left ventricle and the lowest level was found in inflow tracts (atria). B—Schematic diagram of the Col2a1 locus and targeting vector where exon 2 was disrupted by insertion of the Neo gene flanked by loxP sites. The Neo gene was subsequently excised by Cre-mediated recombination. C, D, E—Targeted deletion was confirmed by southern blotting, RT-PCR, and WISH, respectively.

FIG. 6. Cardiovascular Defects in Newborn II−/− Mutants

From left to right, transverse sections are displayed from cranial to caudal ends of the thorax. Panels (A-C) are from WT newborn mice. Panels (D-L) are from IIA$^{-/-}$ mutants. A,B—In WT, the pulmonary artery (p) arises from the right ventricle (rv) and is situated anterior and cranial to the aorta (a). The aorta curves to the left of the trachea (t) and gives rise to right subclavian artery (rs) and right carotid artery (rc), left carotid artery (c), and left subclavian artery (ls). C—An interatrial septum separates the right and left atria (arrowhead) while interventricular septum (ivs) separates the left ventricle (lv) from the right ventricle (rv). Note that right ventricular wall is thinner than that of left. D-F—An example of incomplete TOGA with DORV, and subpulmonic VSD. D—In IIA$^{-/-}$ mutants, the aorta (a), which gives rise to head vessels, is anterior to the pulmonary artery (p). An anomalous coronary artery (asterick) arises from the ascending aorta. E—The aorta (a), where coronary arteries take off (arrows), arises entirely from the RV. A large patent ductus arteriosus (pda) connects to a left descending aorta (da). F—The pulmonary artery (p) is caudal to the aorta and arises both from LV and RV. The pulmonary valve (pv) is overriding a subvalvular ventricular septal defect (arrowhead). G—An example of complete TOGA, where the aorta (a) arises from RV. The pulmonary artery (p) is transposed caudally and posteriorly and arises entirely from LV. H—A large ECD (double arrowheads) I—Persistant trunctus arteriosus (PTA), a complete failure of septation of the primitive outflow tract with resultant main pulmonary arteries (p) arising from the posterior wall of the common arterial trunk and sharing of common abnormal truncal valves (tv). J—A right lateral view of a IIA$^{-/-}$ mutants with right aortic arch and descending aorta (rda) curves to the right of the trachea (t), giving rise to separate right carotid artery (rc), right subclavian artery (rs), and a left carotid artery (lc). A large PDA connects the pulmonary artery and descending aorta (rda). K—Interrupted aortic arch in a IIA$^{-/-}$ mutant. Note that the aortic arch between the left carotid artery (ic) and left subclavian artery (ls) is absent (outlined by broken lines). L—A retro-esophageal left subclavian artery (res) arises from the right descendint aorta (rda) and courses behind the esophagus (e) and trachea.

FIG. 7. Defective BMP signaling in IIA−/− embryos

A—WISH with BMP2 riboprobe in E9.5 IIA−/− embryos (right panel) shows BMP2 expression is diminished in the heart, including the atrioventricular cushion, and proepicardial organ (PEO). B—WISH with BMP4 riboprobe also shows diminished BMP4 expression in the ventricles, atria, and PEO of the IIA−/− embryo (right panel). C—WISH with TGFβ-2 riboprobe shows diminished expression in AV cushion and PEO (right panel). D—Immunohistochemistry against BMP2 protein (upper panels) and BMP4 (lower panels) in E13.5 hearts shows that there is no significant change in protein expression in IIA$^{-/-}$ mutants (right upper and lower panels).

E Immunohistochemistry against phosphorylated Smad1 (p-Smad1) in serial sections from E13.5 embryos. In IIA$^{-/-}$ mutants (third and fourth panels), the number of nuclear staining with p-Smad1 is significantly reduced across the entire heart, especially in the right ventricle (RV) and interventricular septum (IVS). F—Co-localization of IIA, BMP2, and BMP4 proteins in wild-type hearts. In the E8.5 (first row), IIA protein and BMP proteins co-localized in the ECM of both endocardium and myocardium. In the OFT of E9.5 looping heart (second row), BMPs and IIA protein remain colocalized in the ECM of myocardium but BMP expression is lost in endocardial lining. In the primitive left ventricle (third row) of the same heart, BMPs and IIA also colocalize in the ECM of myocardium.

FIG. 8. Defective Nkx2.5 expression in I embryos A WISH with Nkx2.5 riboprobe. At E9.5, there was significant reduction of Nkx2.5 expression in IIA heart (second column). Transverse sections of E9.5 hearts show both reduction in the size of mutant hearts and reduced Nkx2.5 expression in individual cells (fourth column). B —WISH of E8.5 embryos with Col2a1 riboprobe that detects transcription of the gene and recognizes both IIA and IIB mRNAs. In IIA mutant (right panel), reduced signal was detected in the heart despite the fact that targeted deletion of exon 2 of Col2a1 should not affect transcription of the gene. C. Comparative genomics at the Col2a1 locus identifies three conserved non coding regions upstream of the gene using VISTA program. D. One region (region C) contains conservec Nkx2-5, GATA4 and SRF sites. (SEQ ID NOS: 1-18) E. Top- diagram of Col2a1 locus showing the positions of three (regions A, B, C) conserved non-coding sequences upstream of the transcriptional start pf the gene, bSY1 is a modification of the bac clone (61 F08) containing the whole Col2a1 gene with the LacZ gene inserted into exon 1 of the gene. Middle row, X-gal staining of representative bSY1 transgenic embryo showing strong expression in the heart and lower row, bSY2$^{nkx-neo}$ 8.5dpc embryos. In the bSY1 embryo, intense blue staining in the heart recapitulates endogenous Col2a1 expression pattern. Bottom row, in the bSY2$^{nkx-neo}$ 0embryo, deletion of Nkx2.5 binding site in the 5regulatory region of Col2a1 by inserting the neo gene into the Nkx2.5 site results in abolishment of lacZexpression in the heart.

FIG. 9. Summary of roles of IIA procollagen in Nkx2.5 regulatory loop during cardiovascular morphogenesis Once a contractile, linear heart tube is established, looping and lengthening of OFT involve further addition of cardiac progenitor cells from the cardiac crescent and anterior heart field and finally participation by cardiac neural crest cells. At this stage, a regulatory loop is initiated where Nkx2.5 enhances or maintains IIA procollagen production by regulating the Col2a1 gene. IIA procollagen in turn acts as facilitator, sequesters BMP2 ligands, presents the morphogen to BMP receptors, and thus augments BMP signaling necessary for deployment of these progenitor cells. Note that it is not known if IIA procollagen and BMP complexes are processed by proteases (such as furin-like, tolloid) to release the BMP for interaction with the receptor. Nuclear translocation and binding of BMP-responsive phosphorylated smads—Co-smad 4 complexes to the smad responsive element on the 5' regulator region of Nkx2.5 promotes transcription and translation of Nkx2.5. Nkx2.5 in turn activates Col2a1 and thus a regulatory loop is completed. This regulatory loop potentially also involves combinatorial interactions of GATA and SRF transcription factors. It is known that GATA4 and Smad4 cooperatively transactivate Nkx2-5 and GATA6 has been shown to regulate Nkx2-5 (reviewed in Patient R K, McGhee, J D, Curr Op Gen Dev 12:416-422 (2002); Peterkin T et al Sem Cell Dev Biol 16: 83-94 (2005). Nkx2-5 has also been shown to regulate GATA6 in a reinforcing regulatory network {Molkentin, J. D. et al. Direct activation of a GATA6 cardiac enhancer by Nkx2.5: evidence for a reinforcing regulatory network of Nkx2.5 and GATA transcription factors in the developing heart. Dev Biol 217, 301-9 (2000).}. SRF can interact with GATA4 or Nkx2-5 to activate genes in cardiomyocytes. Note the presence SRF, GATA and Nkx2-5 bindng sites in the conserved Col2a1 enhancer element (FIG. 8.C-D).

DETAILED DESCRIPTION OF THE INVENTION

During mouse embryogenesis, the mouse a1(II) collagen gene (Col2a-1) is transiently expressed in many non-cartilaginous tissues such as the notochord, neural retina, tail tendon, heart, surface ectoderm, calvarial mesenchyme, fetal brain, the sensory epithelium of the inner ear and the apical ectodermal ridge of the forming limb buds. Alternative splicing of exon 2 produces type II procollagen mRNAs that either include (IIA mRNA) or exclude (IIB mRNA) this exon. Type IIA mRNA is abundant in cells of the epimyocardium in both the atria and ventricles of 9.5-day embryos but rapidly diminishes by 10.5 days. After 12.5 days, IIB mRNA levels increase rapidly and finally-exceed IIA mRNAs. By 16.5 days, IIB mRNAs are the major Col2a-1 transcripts predominantly expressed in maturing chondrocytes.

To understand the function of IIA, gene targeting was used in embryonic stem cells to produce mutant mice that can only produce Col2a-1 mRNA without exon 2. Compelling evidence showed that IIA plays an essential role in cardiac morphogenesis by modulating BMP and TGFβ signaling. Mice lacking IIA display multiple cardiovascular malformations with many features of some human congenital heart diseases. Because of the variable penetrance of the severe phenotype, the IIA mutants were backcrossed to the C57B16 background (6 generations). The genetic background of these IIA−/− mutants was predominantly C57/BL6 background (approximately 90-95%) with a small contribution of 129Sv and ICR background. Mice homozygous for the IIA null mutation (IIA−/−) display defects in patterning and morphogenesis of the heart similar to those associated with loss of function of the BMP, TGF-β and nodal signaling pathways and die perinatally from cardiovascular insufficiency. The spectrum of heart defects include ventricular septal defect (VSD), patent ductus arteriosus (PDA), persistent truncus arteriosus (PTA), right ventricular hypertrophy, right aortic arch with or without anomalous origins of subclavian arteries, and the Double Outlet Right Ventricle (DORV) where aorta and pulmonary arteries arise wholly or in great part from the right ventricle, with associated VSD, transposition of great arteries (TOGA), and endocardial cushion defects with primum atrial septal defects. Both BMPlTGFβ signaling activity and expression of Nkx2.5 were reduced in the IIA mutant hearts. We show that Nkx2.5 regulates the Col2a-1 gene, which was reciprocally down-regulated in Nkx2.5-null mutants. Our findings highlight a novel role for extracellular matrix proteins such as procollagen IIA which regulates cardiovascular morphogenesis by modulating cardiac transcription factors activity through a BMP-mediated signaling via a regulatory loop. Procollagen IIA deficiency may underpin some common congenital heart diseases. The majority of mutant embryos have a triad of DORV, incomplete TOGA, and subpulmonic VSD, the findings consistent with Taussig-Bing anomaly in humans. Taussig-Bing anomaly is a rare but severe complex cyanotic congenital heart disease, first described by Pernkopf in 1920 and subsequently by Helen Taussig and Richard J. Bing in 1949.[30] Its mode of genetic transmission and molecular defects have not been systematically studied. This line of IIA mutant therefore may be useful as a novel animal model of Taussig-Bing anomaly.

In generating these IIA null mutants, a viable line of IIA7- mice (hereafter referred to as 191-IIA) with a mixed genetic background comprising C57/BL6; 129Sv; ICR was also generated. It is at the 5$^{th}$ generation of homozygous matings. In the second generation, 12 out of 19 animals died shortly after birth. Out of 28 animals in the third generation, 6 died prematurely between 2 to 8 months. Interestingly, there was a preponderance of males among those showing premature death (FIG. 1). The following observations were made from limited necropsy:

Cardiomegaly with atrial enlargement and increased wall thickness in right and/or left ventricles (FIG. 1, 2C, 2D)
Hypercellularity with atypical nuclei, mostly in interstitium (FIG. 2F, 4A-C)
Cardiomyocyte disarray and heterogeneity in size, with prominent cellular hypertrophy (FIG. 2F, 4A-D)
Valvular fibrosis (FIG. 3B,D)
Absence of extensive myocardial necrosis or fibrosis Absence of outflow tract or aortic arch anomalies The severity of cardiomyocyte hypertrophy and disarray seems to correlate with shortened survival (compare FIG. 2F with FIG. 4A, B, and D).

These adult 191Co/IIA−/− mice develop cardiomyopathy because of dysregulation in cardiomyocyte proliferation and growth during fetal and/or postnatal development. One possible mechanism is that the absence of IIA procollagen at a critical period of heart morphogenesis perturbs the delicate balance among different collagen isoforms and alters the extracellular matrix composition in fetal/neonatal/adult hearts. Of note, exon 2 of the type II collagen gene (Col2a-1), which is included in IIA mRNA, encodes a cysteine-rich globular domain that has been shown to bind bone morphogenic proteins (eg. BMP2) and Transforming Growth Factor (TGF)-β1 in in vitro assays. This alteration in the cardiac matrix in turns may perturb the proper local gradients of BMP2 and TGF-β and may alter cardiomyocyte contractility by affecting sarcomeric assembly and/or signal transduction.

Clinical studies have demonstrated that cardiac hypertrophy is a major risk factor for major cardiac events, such as myocardial infarction, heart failure, sudden cardiac death, and stroke.[31,33] This line of mutant mice can be used to screen potential drugs for the treatment of cardiac hypertrophy, a major risk for sudden death and heart failure. For example, one may administer drug X or a placebo to adult 191-IIA mice. After 4 weeks of treatment, both groups of 191-IIA mice are sacrificed and examined for the extent of change in cardiac hypertrophy by histological techniques. The myocardial infarction induced in this line of mutant mice will be useful as a platform to screen for potential drugs against ventricular remodeling and malignant arrhythmias. In this case, coronary arteries of 191-IIA. mice are ligated to induce myocardial infarction. One group receives drug X and the other a placebo. Both groups have implantable telemetry to evaluate for the occurrence of malignant arrhythmias. Both groups have serial echocardiography to evaluate for any changes in cardiac function. At the end of the drug treatment, both groups are sacrificed and their hearts are processed by paraffin embedding, serial sectioning, Hematoxylin and Eosin stainings, and trichrome Mason's stainings. These cardiac sections are examined for the geometric changes associated with ventricular remodeling as well as cellular disarray and hypertrophy.

Roles of TGF-Beta and BMP Signalings in Development of Cardiomyopathy:

Of note, exon 2 of the type II collagen gene (Col2a-1), which is included in IIA mRNA, encodes a cysteine-rich globular domain in the amino-propeptide of pro-α1(II) collagen chains. This cysteine-rich domain has been shown to bind Bone Morphogenetic Proteins (e.g. BMP2, BMP4, BMP7) and Transforming Growth Factor (TGF)-β1 in in vitro assays. Members of the TGFβ superfamily and downstream effectors have been shown to play crucial roles in various aspects of heart development (examples in Table 1), especially in cardiomyocyte differentiation, valvulogenesis, and outflow tract and septal development. TGF-β1 exerts diverse biological activities in postnatal hearts. It controls the expression of major histocompatibility complex, induces production of the extracellular matrix proteins by cardiac fibroblasts, regulates vascular smooth muscle cell phenotype, induces cardiac hypertrophy, and enhances β-adrenergic signaling. There is limited information about the role of BMPs in postnatal mammalian hearts. In rat neonatal cardiomyocyte culture, BMP-2 exerts antiapoptotic effect by activation of the Smad1 pathway and enhances contractility by activation of phosphatidylinositol 3 kinase pathway. The adult 191-IIA mutant mice are therefore a very important model for cardiomyopathy secondary to the dysregulation in BMP/TGF signaling. The 191-IIA mutants are useful models to screen potential drugs, whether it be pharmaceutical or gene therapy, targeted at the BMP/TGF induced Smad signaling pathways on cellular hypertrophy and proliferation. Such drug candidates can be ligand traps, BMP or TGF-β agonists, receptor antagonists, or Smads proteins. The end-points of such drug testing will be (1) amelioration or abrogation of cardiac hypertrophy and (2) improved survival.

Roles of TGF-Beta and BMP Signaling in Primary Pulmonary Hypertension:

Primary pulmonary hypertension (PPH) is a progressive and fatal disease where mean pulmonary arterial pressure at rest is greater than 25 mmHg or 30 mmHg with exertion in the absence of left-sided heart diseases, chronic thromboembolic disease, underlying pulmonary diseases, or other secondary causes. It is a rare disorder that commonly affects young people, especially women in the third decade of life, leading to progressive right heart failure and death with the median survival of 2.8 years. PPH is characterized by obstruction of small pre-capillary pulmonary arteries with associated plexiform lesions, medial hypertrophy, intimal fibrosis, fibroid degeneration, and thrombotic lesions. Symptoms associated with primary pulmonary hypertension are often non-specific, including dyspnea, palpitations, fatigue, chest pain, near-syncope, syncope, peripheral edema, and as a result, the correct diagnosis is often delayed. Standard therapies include anticoagulation, calcium channel blockers, prostacyclin infusion, and, in refractory cases, lung transplantation and atrial septostomy. Other pharmacological agents in trial include inhaled or oral prostacyclin analogues, phosphodiesterase inhibitors, endothelin-1 receptor antagonists, and L-arginine. Central pathogenesis is thought to involve dysregulation in smooth muscle and endothelial cell proliferation rather than abnormal vasoconstriction.[34] Genetic analysis reveals that deleterious heterozygous mutations in type II receptors for BMP (BMPR2) are present within the majority of familial and up to 26% of sporadic cases of primary pulmonary hypertension.[24,25,35] In addition, in 9% of patients who developed pulmonary hypertension after exposure to appetite suppressant fenfluramine and dexfenfluramine are found to have mutations in BMPR2.[36] More recently, mutations in ALK-1, a component of TGF-β receptors, are found most commonly in patients with hereditary hemorrhagic telangiectasia and pulmonary hypertension.[37]

Many experimental data have demonstrated the pivotal roles that defective TGF-β and BMP signaling play in the pathogenesis of pulmonary hypertension. For examples, transgenic mice expressing dominant-negative BMPR2 in smooth muscles develop pulmonary hypertension.[38] While BMP-2 enhances apoptosis of normal human pulmonary vascular smooth muscle cells, primary arterial smooth muscles from PPH patients exhibit abnormal growth responses to BMP and TGF-p.[39,40] In one embodiment, the 191-IIA mice will serve as a stand model of PPH to screen for potential drugs, whether it be pharmaceutical or gene therapy, targeted at the BMP/TGF induced Smad signaling pathways in pulmonary vascular smooth muscle cells and endothelial cells. Such drug candidates can be ligand traps, BMP or TGF-P agonists, receptor antagonists, or Smads proteins. The end-points of such drug testing will be (1) amelioration or abrogation of pulmonary pathology found in PPH (i.e., plexogenic or thrombotic arteriopathy), (2) amelioration or abrogation of right ventricular hypertrophy, and (3) improved survival.

Roles of TGF-Beta and BMP Signaling in Valvular Fibrosis:

The transient absence of IIA collagen during the critical period of embryonic development results in fibrosis of semilunar and atrioventricular valves. Studies in recent years have clearly established the critical roles of TGF-β and BMPs in valvulogenesis during development. Currently, surgical repair, valve replacement, and balloon valvulotomy remain the only treatment options for aortic stenosis and mitral stenosis, both which present with fibrotic, often calcified valves with decreased leaflet mobility. The 191-IIA mice will serve as stand model to develop novel non-surgical therapeutics for treatment of degenerative valvular diseases. Drugs targeted at TGF-β and BMP signaling pathways will be administered to the 191-IIA mice and screened for their anti-fibrotic effects.

Characterization of the Hemodynamic Alteration and Determine the Mechanisms of Sudden Death in Adult 191Co/IIA−/− Mice:

1) Postmortem Analysis of Adult 191Co/IIA−/−Mice that Died Suddenly
   a) Light Microscopy
   Paraffin blocks of the heart, lungs, and aorta are sectioned along specific axes of the heart, processed for H& E stainings and Mason's trichrome stainings and analyzed for inflammatory infiltration, pathological hypertrophy, and interstitial fibrosis.
   b) Electron Microscopy
   The cardiac sections are examined by transmission electron microscopy to delineate any ultrastructural defects in the myofibrils and extracellular matrix.

2) Cardiovascular Functional Assessment
   Cardiomegaly found in 191 Co/IIA−/− mice could be caused by myocyte hypertrophy, hyperplasia, myocardial fibrosis with chamber dilatation, or infiltrative disease. In order to define the clinical course of cardiomegaly and elucidate the mechanisms of sudden death, we plan to study 191Co/IIA−/− mice and wild-type littermates in parallel. Heterozygous 191Col-IIA+/− mice are generated by one round of backcrossing 191 191ColIIA−/− mice with 1CR mice. Wild type littermates are derived by heterozygous matings. Since the mode of sudden death may be different for different age groups, the following studies will be conducted at 2 months and 8 months of age.
   a) Determination of Chamber Sizes and Function by Echocardiography
   (ECHO) Serial transthoracic ECHO will be performed to determine the left and right ventricular chamber size, wall thickness, systolic function, and presence of significant valvular diseases.
   b) Evaluation for Systemic Hypertension
   Hypertrophy, fibrosis, or chamber dilatation may be manifestations of hypertensive heart disease or valvular diseases. Serial blood pressure measurement are obtained using the cuff-tail method. This non-invasive method allows one to follow these mice longitudinally for development of hypertension.
   c) Evaluation for Cardiac Arrhythmias
   By mechanisms that are yet to be defined, hypertrophy, fibrosis, and poor left ventricular function often lead to malignant arrhythmias that are major causes of sudden cardiac death. To rule out malignant arrhythmias as potential causes of sudden death, the heart rhythm of IIA−/−mice and wild type littermates is monitored with a miniature telemetric device from Data Sciences International.
   d) Determination of Left Ventricular Contractility and Compliance
   Any change in the extracellular matrix composition and the architecture of cardiomyocytes will invariably affect global contractile performance of the heart. To determine any alteration in systolic contractility and diastolic compliance, left ventricular pressure-volume loops will be generated using the specialized conductance catheter from Millar in non-recovery surgery.
   e) Evaluation for Pulmonary Hypertension
   One consistent finding among these IIA−/−mice with premature death is increased right ventricular wall thickness. Combination of hypercellularity and hypertrophy may explain this finding. Right ventricular hypertrophy may be a manifestation of primary myocardial disease, or secondary to pulmonary hypertension. To rule out pulmonary hypertension, pulmonary artery pressure is measured directly by inserting a single-lumen catheter (0.25 mm O.D.) with a curved tip from the right jugular vein through the right atrium, tricuspid valve, and right ventricle into the main pulmonary artery. Lung sections are examined for microscopic changes associated with pulmonary hypertension, such as medial hypertrophy of airway vasculature and pulmonary fibrosis.

Determination of the Cellular and Molecular Defects in the Hearts of Adult ColIIA−/− mice.

Murine cardiomyocytes continue to proliferate at a low rate during first three weeks after birth.[42] More recent morphometric analysis has confirmed that mouse cardiomyocytes continue to divide for the first 4 postnatal days and increase in the volume between days 5 and 14. After day 14, individual cardiomyocytes continue to increase in volume, albeit at a slower rate, and finally reaches the adult size at 3 months of age.[43] It is possible that this transition point from proliferation to developmental growth has shifted in 191 ColIIA−/− mice. Therefore, this part of study focuses on adult mice at 2, 5, and 8 months of age. If cardiomyocyte hypertrophy is a prominent feature, the hearts are examined from earlier time points to determine when pathological hypertrophy starts after birth. All the reagents for sections (1), (2), and (4) are commercially available. Antibodies for the characterization of the extracellular matrix proteins are either commercially available or available through our overseas colleagues.

1) Cardiomyocyte Hypertrophy
   a) Morphometric Analysis
   i) Increased wall thickness could be due to increase in cardiomyocyte size (hypertrophy), increase in density (hyperplasia) of myocytes and/or nonmyocytes, and/or increase in interstitial space from infiltrative process. To determine whether myocyte hypertrophy is present, HA−/− mice and their sex-matched wild type litternates will be sacrificed at 2 months, the body and heart weights, and tibial lengths determined. The LV or RV/body weight ratio and LV/RV ratio will be determined. For histological analysis, 1 mL of cadium chloride 0.1 M will be infused into the inferior cava to achieve cardiac arrest in diastole and the animal will be retrogradely perfused with phosphate buffered saline at 100 mmHg followed by perfusion with 3.7% formalin. The arrested heart will be fixed for 2 hours to 24 hours in 4% paraformaldehyde and embedded in paraffin for sectioning.
   ii) To determine the density and size of cardiomyocytes, heart sections will be processed for double immunofluorescent labeling with FITC-laminin antibody, which outlines the cardiac sarcolemma, and propidium iodide (PI). To determine the dimensions and volume of individual cardiomyocytes from left and right ventricles, individual cardiomyocytes will be isolated using the method developed by Leu and co-workers.[43] Briefly, a strip of myocardium from either left or right ventricle will be tied to a board and collagenase digestion will be carried out in the presence of verapamil, a calcium channel blocker. By triturating gently, individual cardiomyocytes are released as rod-shaped cells. These cells will be plated on gelatin-coated slides and processed for immunofluorescence labeling with sarcomeric alpha-actin antibody. The arrangement as well as density of sarcomeres per cell will be determined. This method also allows selective isolation of cardiomyocytes from right ventricles and will be extremely useful in assessing the presence of cellular hypertrophy in these cells.

iii) The cellular volume is measured using laser confocal microscopy and 3-D image reconstruction program.

b) Alterations in Contractile Proteins

The levels of myosin heavy chain, myosin light chain, tropomyosin, troponin T, and actin are analyzed by immunoblotting of heart lysates.

c) Reactivation of "Fetal" Genes

Pressure-overload induced cardiac hypertrophy is associated with reactivation of "fetal" genes. Therefore, the expression of ANP, BNP, α-skeletal actin, β-MHC, and SERCA by quantitative RT-PCR.

d) Hypertrophic Signaling Pathways

Mitogen-activated protein (MAP) kinases are one of the major mediators of cardiac hypertrophy. Activation of MAPK pathway, which involves phsophorylation of p38 MAPK. ERK1/2, and .INK, is determined by Western blot analysis.

e) Apoptosis

One possible explanation for the postmortem findings is that cardiomyocyte apoptosis and cell cycle regulation are altered. Hypertrophy may occur as a compensatory reaction to apoptosis. To determine whether apoptosis is enhanced in adult IIA−/− mice, in situ TUNEL staining will be done on the heart sections of two-month old mice.

2) Hyperplasia a) Myocyte vs. nonmyocyte

If PI staining indicates increased density, we will identify the proliferating fibroblasts, myofibroblasts, and cardiomyocytes by dual labeling with vimentin, smooth muscle alpha-actin, or sarcomeric alpha-actin antibodies, respectively.

b) Cardiomyocyte Hyperplasia i) In case of cardiomyocyte hyperplasia, the question is whether the cardiomyocyte DNA synthesis and mitoses are enhanced in the adult 191Co/IIA−/− mice. BrdU is injected intraperitoneally into 2-month old mice 4 hours before euthanasia and the hearts will be processed for indirect immunofluorescent labeling with anti-BrdU and anti-sarcomeric MHC (MF20) antibodies. In addition, mitotic cells is identified by using phospho-histone H3 monoclonal antibody.

ii) If cardiomyocyte hyperplasia is present, a permanent cell line is isolated and established by enzymatic dissociation of cardiomyocytes from adult IIA−/−hearts. Such a cell line is a useful tool to study the cell cycle regulation incardiomyocytes.

3) Alterations in the Cardiac Extracellular Matrix

Given the presence of left and/or right ventricular hypertrophy, it is imperative to determine whether there is any change in collagen total content, isoforms, and distribution in the heart. Because alterations in the composition of cardiac extracellular matrix may be present at birth or may be in response to mechanical stress, both newborn and adult myocardiums are examined. Antibodies for the characterization of the extracellular matrix proteins are either commercially available or available through our overseas colleagues.

a) Collagen Content and Isoforms i) Total collagen content in the left ventricle, septum, and right ventricle are determined separately by measuring the hydroxyproline concentration.

ii) Spatial distribution and protein expression levels of types I-V, and VI are determined by immunohistochemistry.

iii) Distribution patterns of type I and III collagen by Sirius red-polarization method. When the heart section is stained with Sirius red, type I collagen appears as thick, strongly birefringent, yellow or red fibers while type III collagen appears as thin, weakly birefringent green fibers.

iv) Transmission electron microscopy confirms the findings from Sirius Red method and allows for the examination of the relationship between various components of extracellular matrix and surrounding cells at the highest resolution.

v) To determine whether types I and III collagen content is altered because of type IIA deletion, quantitative real-time TaqMan RT-PCR is performed at various time points. As mRNA may not reflect protein levels or even expression, Western Blot analysis is performed from cardiac lysates to correlate the expression levels between the transcript and protein.

vi) To determine whether there is abnormal ectopic expression of type IIB procollagen in the postnatal hearts, Western blot analysis is performed using type II collagen antibody. In the IIA−/− mice, immunoreactive bands indicate the exclusive presence of IIB procollagen.

b) Distribution of Non-Collagen Components

The distribution and expression levels of laminin, fibrillins, proteoglycans (biglycan, decorin, and fibromodulin) and fibronectin is examined by immunohistochemistry, in situ hybridization, Western blots, and quantitative RT-PCR.

4) Integrity of TGF-β/BMP Signaling Pathways in Adult Myocardium a) TGF-β Isoform Expression Recent human and animal studies have shown that myocardial TGF-β1-3 is increased in the setting of cardiac hypertrophy and myocardial fibrosis. Therefore, if hypertrophy or fibrosis is present, quantitative PCR is performed to determine the time course and magnitude-of TGF-β elevation as well as immunohistochemistry to localize TGF-β isoform expression in the interstitium.

b) Because the BMP2 and TGF-β1 binding cysteine-rich domain is lost as a result of targeted deletion of ColIIA gene, it is mechanistically important to determine whether the adult cardiac pathology is a consequence of derangement in TGF-β/BMP signaling pathways.

i) Protein expression level, phosphorylation status of Smads 1/5/8 or 2/3, and nuclear translocation is determined by Western blot analysis of cardiac cytoplasmic and nuclear isolates with the antibodies against total or phosphorylated forms of Smads 1/5/8 or Smads2/3.

ii) Immunohistochemistry with the same sets of phospho-Smads antibodies are performed on adult cardiac sections from IIA−/− and +/+ littermates to demonstrate nuclear translocation of phospho-Smads 1/5/8 or phospho-Smads2/3 and Co-Smad4 complex. Analysis will focus on the prevalence of nuclear co-localization in relation to the presence of myocardial hypertrophy/hyperplasia. If no nuclear co-localization is detected, the expression levels of type 1 and II receptors (TpR-II, BMPR-I1, ALK 1-2,3,5, and 6), Co-Smad 4, and inhibitory Smads 6 and 7 in the hearts of affected and non-affected adult 191 ColIIA-/- mice are determined by quantitative PCR and immunoblotting.

In addition to potential defects at the intracellular level, access of TGF-β1 and BMP-2 ligands to their specific receptors may be affected by a large family of proteins known as ligand traps.

5) Microarray Analysis to Define the Mechanisms of Cardiomyopathy

In order to understand the molecular events leading to these cardiac defects, microarray technology is used to analyze the pattern of gene expression in 191 ColII A-/- hearts. In addition to alteration in TGF/BMP signaling pathways, many classes of genes are affected in 191 Co/IIA-/- hearts, including genes encoding for extracellular matrix proteins, cell cycle regulators, contractile and cytoskeletal proteins, ion channels, and muscle-specific transcription factors. The microarray technology is chosen over the candidate gene approach because the former allows genome-wide screening for alteration in many mRNAs simultaneously in a highly efficient and quantitative manner. Microarray analysis in this instance can determine the complex interaction between the extracellular matrix and cardiomyocytes. Time-dependent changes in gene expression profiles are of interest as well as chamber-specific changes. Gene expression profiles are examined at three different time points: Embryonic day 15.5, neonatal period 1 week, and young adult period (2 months). These three time points are chosen because at E15.5, cardiac morphogenesis has completed and there is a clear anatomical separation of the left ventricle from right ventricle. There is a major hemodynamic alteration at birth and isoform switching occurs in major contractile proteins in response to this hemodynamic shift. However, because murine cardiomyocytes continue to proliferate at a low rate during first three weeks after birth, the gene expression profile is examined beyond this transition point from proliferation to developmental growth. Because chamber specification (i.e., left versus right ventricles) is transcriptionally regulated by different sets of genes and because there is prominent right ventricular hypertrophy in 191 ColIIA-/- mice, the gene expression profiles is compared between the left and right ventricles at these three time points. (Example: Table 2)

TABLE 2

| Group | Embryonic Day 15.5 | Postnatal Day 3 | Adult 2 month |
|---|---|---|---|
| Wild type | Left ventricle | Left ventricle | Left ventricle |
| 191 Co/IIA-/- | Left ventricle | Left ventricle | Left ventricle |
| Wild type | Right ventricle | Right ventricle | Right ventricle |
| 191 Co/I IA-/- | Right ventricle | Right ventricle | Right ventricle |

Thus, this invention provides a method for producing a mutant procollagen IIA (Col2A-1) transgenic mouse comprising the steps of: a) introducing into mouse embryonic stem cells a gene-targeting vector comprising a mutant Col2A-1 transgene which is to replace a corresponding endogenous homologous gene by homologous recombination in the mouse embryonic stem cell; b) selecting for the mouse embryonic stem cells of step (a) which contain the mutant Col2A-1 transgene; c) introducing the mouse embryonic stem cells selected in step (b) into mouse blastocysts or aggregating the mouse embryonic stem cells selected in step (b) with mouse morula; d) transplanting the mouse blastocysts or aggravated morula of step (c) into a pseudopregnant mouse, thereby forming an embryo; e) allowing the embryo of step (d) to develop to term, thereby producing a chimeric founder transgenic mouse; and f) crossing the chimeric founder transgenic mouse of step (e) with a wildtype mouse, thereby producing a mutant Col2A-1 transgenic mouse. The mutant Col2A transgene lacks exon 2 which encodes a cysteine-rich binding domain for BMP-2 or TGF-β1. This invention further provides the above-described transgenic mouse.

This invention further provides a method of producing a null mutant mouse (IIA-/-) comprising backcrossing of the mutant Col2A-1 transgenic mouse with an inbred strain (C57BL6) of mouse. The null mutant mouse displays multiple cardiovascular malformations, features of human congenital heart defects or defects in patterning and morphogenesis of the heart similar to those associated with loss of function of the BMP, TGFβ and nodal signaling pathways. The complex heart defects include ventricular septal defect (VSD), patent ductus arteriosus (PDA), persistent truncus arteriosus (PTA), right ventricular hypertrophy, right aortic arch with or without anomalous origins of subclavian arteries, and the Double Outlet Right Ventricle (DORV) where aorta and pulmonary arteries arise wholly or in great part from the right ventricle, with associated VSD, transposition of great arteries (TOGA), anomalous coronary arteries, and endocardial cushion defects with primum atrial septal defect. This line of mutant mice represents a novel genetic model of Taussig-Bing anomaly, a rare but severe complex cyanotic heart disease in humans. This invention further provides the above-described transgenic mouse. The above-described transgenic mouse may be a strain of mouse designated 191-IIA or a transgenic mouse with similar phenotypes. Such phenotypes include hypertrophy of left or right ventricules, cardiomyocytes enlargement and disarray, hypercellularity with atypical nuclei, valvular fibrosis, and absence of extensive myocardial necrosis outflow tract abnormality, and branchial arch anomalies.

This invention further provides a method of determining agents for treatments of cardiac disorders using 191-IIA mice comprising the steps of: a) administering the agent to a first group of adult 191-IIA mice; b) administering a placebo to a second adult 191-IIA mice; c) measuring one or more of the following symptoms for the group of step (a) and the group of step (b): cardiac hypertrophy, cardiac hyperplasia, valvular fibrosis, cardiac function, serial blood pressures and heart, malignant arrhythmias and time-dependent changes in gene expression profiles in right and left ventricles; and d) comparing the measurements of step (c) in order to determine whether the agent treats the cardiac disorder. The treatments may be pharmaceutical and gene therapies that are targeted at the BMP/TGF related molecules and induced Smad signaling pathways on cellular hypertrophy. The agent can be naturally occurring compounds or their purified derivatives, synthetic compounds, ligand traps, BMP or TGF agonists, receptor antagonists, Smad family proteins, or viral or non-viral vectors.

This invention also provides a cell line derived from the heart tissues of a 191IIA mouse or those of IIA-/- mouse embryos.

This invention also provides a method of using procollagen IIA or its derivatives to titrate the expression level of a key cardiac transcription factors such as Nkx2.5 and GATA4 in embryonic cardiomyocytes.

REFERENCES

1. Zheng Z J, Croft I B, Giles W H, Mensah G A. *Circulation* 2001; 104:2158-63.
2. Virmani R, Burke A P, Farb A. *Cardiovascular Pathology* 2001; 10:211-218.
3. Maron B J, McKenna W J, Danielson G K, et al. *Journal of the American College of Cardiology* 2003; 42:1687-1713.
4. Maron B J. *N. Engl. J. Med.* 2003; 349:1064-1075.
5. Fatkin D, Graham R M. *Physiol. Rev.* 2002; 82:945-80.
6. Weber K T, Sun Y, Tyagi S C, Cleutjens J P. *J. Mol. Cell. Cardiol.* 1994; 26:279-92.
7. de Souza R R. *Biogerontology* 2002; 3:325-35.
8. Medugorac I. *Res. Exp. Med.* (Bed) 1980; 177:201-11.
9. Honda M, Yamada S, Goto Y, et al. *Jpn. Circ. J.* 1992; 56:392403.
10. Gardi C, Martorana P A, Calzoni P, et al. *Experimental and Molecular Pathology* 1994; 60:100-107.
11. Cheah K S, Au P K, Lau E T, Little P F, Stubbs L. *Maram Genome* 1991; 1:171-83.
12. Wood A, Ashhurst D E, Corbett A, Thorogood P. *Development* 1991; 111:955-68.
13. Rahkonen O, Savontaus M, Abdelwahid E, Vuorio E, Jokinen E. *Histochem. Cell. Biol.* 2003; 120:103-10.
14. Potocki L, Abuelo D N, Oyer C E. *Am. J. Med. Genet.* 1995; 59:295-9.
15. Zhu Y, Oganesian A, Keene D R, Sandell L J. *J. Cell. Biol.* 1999; 144:1069-80.
16. Shi Y, Massague J. *Cell* 2003; 113:685-700.
17. Zwijsen A, Verschueren K, Huylebroeck D. *FEBS Lett* 2003; 546:133-9.
18. Delot E C, Bahamonde M E, Zhao M, Lyons K M. *Development* 2003; 130:209-20.
19. Keyes W M, Logan C, Parker E, Sanders E J. *Anat. Embryol.* (Berl) 2003.
20. Monzen K, Nagai R, Komuro I. *Trends Cardiovasc. Med.* 2002; 12:263-9.
21. Schlange T, Andree B, Arnold H H, Brand T. *Mech. Dev.* 2000; 91:259-70.
22. Izumi M, Fujio Y, Kunisada K, et al. *J. Biol. Chem.* 2001; 276:31133-41.
23. Ghosh-Choudhury N, Abboud S L, Chandrasekar B, Ghosh Choudhury G. *FEBS Lett* 2003; 544:1814.
24. Atkinson C, Stewart S, Upton P D, et al. *Circulation* 2002; 105:1672-8.
25. Machado R D, Pauciulo M W, Thomson J R, et al. *Am. J. Hum. Genet.* 2001; 68:92-102.
26. Kaartinen V, Warburton D. *Nat. Genet.* 2003; 33:331-2.
27. Neptune E R, Frischmeyer P A, Arking D E, et al. *Nat. Genet.* 2003; 33:407-11.
28. Yoshikane H, Honda M, Goto Y, Morioka S, Ooshima A, Moriyama K. *Jpn. Circ. J.* 1992; 56:899-910.
29. Liu X, Wu H, Byrne M, Krane S, Jaenisch R. *PNAS* 1997; 94:1852-1856.
30. Taussig H B B, R J. *American Heart Journal* 1949; 37:551-559.
31. Haider A W, Larson M G, Benjamin E J, Levy D. *J. Am. Coll. Cardiol.* 1998; 32:1454-9.
32. Harjai K J. *Ann. Intern. Med.* 1999; 131:376-86.
33. Verdecchia P, Carini G, Circo A, et al. *J. Am. Coll. Cardiol.* 2001; 38:1829-35.
34. Runo J R, Loyd J E. *The Lancet* 2003; 361:1533-1544.
35. Deng Z, Morse J H, Slager S L, et al. *Am. J. Hum. Genet.* 2000; 67:737-44.
36. Humbert M, Deng Z, Simonneau G, et al. *Eur. Respir. J.* 2002; 20:518-23.
37. Harrison R E, Flanagan J A, Sankelo M, et al. *J. Med. Genet.* 2003; 40:865-71.
38. West J, Fagan K, Steudel W, et al. *Circ. Res.* 2004.
39. Zhang S, Fantozzi I, Tigno D D, et al. *Am. J. Physiol. Lung Cell. Mol. Physiol.* 2003; 285:L740-54.
40. Morrell N W, Yang X, Upton P D, et al. *Circulation* 2001; 104:790-5.
41. Champion H C, Bivalacqua T J, Greenberg S S, Giles T D, Hyman A L, Kadowitz P J. *Proc. Natl. Acad. Sci.* USA 2002; 99:13248-53.
42. Cluzeaut F, Maurer-Schultze B. *Cell Tissue Kinet.* 1986; 19:267-74.
43. Leu M, Ehler E, Perriard J C. *Anat. Embryol.* (Berl) 2001; 204:217-24.

---

What is claimed:

1. A method of producing a mouse homozygous for the mutated type II procollagen alpha-1 (Col2a-1) gene comprising the steps of:
   a) introducing into mouse embryonic stem cells a gene-targeting vector comprising a mutant Col2a-1 mouse gene which has exon 2 deleted but still comprises the remaining coding sequence for the wildtype Col2a-1 mouse gene;
   b) selecting for the mouse embryonic stem cells of step (a) wherein the endogenous Col2a-1 gene has been replaced by the mutant Col2a-1 mouse gene;
   c) introducing the mouse embryonic stem cells in step (b) into mouse blastocysts or aggregating the mouse embryonic stem cells selected in step (b) with a mouse morula;
   d) transplanting the mouse blastocysts or aggregated morulas of step (c) into a pseudopregnant mouse;
   e) allowing the blastocyst or morulas of step (d) to develop to term, thereby producing a chimeric founder mouse;
   f) crossing the chimeric founder mouse of step (e) with a wildtype mouse to produce a mouse heterozygous for the mutated Col2a-1 gene comprising in its genome a Col2a-1 gene that lacks exon 2 but still comprises the remaining coding sequence of the Col2a-1 gene and a wild-type Col2a-1 gene; and
   g) crossing mice heterozygous for the mutated Col2a-1 gene of step (f), thereby producing a mouse homozygous for the mutated Col2a-1 gene comprising in its genome a homozygous mutation of the Col2a-1 gene, wherein the mutated Col2a-1 gene lacks exon 2 but still comprises the remaining coding sequences of the Col2a-1 gene, wherein said mouse homozygous for the mutated Col2a-1 gene expresses a mutant Col2a-1 protein encoded by the mutant Col2a-1 gene, and displays multiple cardiovascular malformations similar to malformations present in human congenital hear defects, defects in morphogenesis of the heart similar to those associated with a loss of BMP, TGF-beta, and nodal signaling pathways including ventricular septal defect (VSD), patent ductus arteriosus (PDA), persistent truncus arteriosus (PTA), right ventricular hypertrophy, right aortic arch with or without anomalous origins of subclavian arteries, and a double outlet right ventricle (DORV) where aorta and pulmonary arteries arise wholly or in great part from the right ventricle, with associated VSD, transposition of great arteries (TOGA), anomalous coronary arteries, or endocardial cushion defect with primum atrial septal defect.

2. A method for producing a mouse comprising a mutated Col2a-1 gene comprising backcrossing the mouse homozygous for the mutated Col2a-1 gene of claim 1 with an outbred stain of mouse.

3. A method of screening agents for treatment of cardiac disorders comprising the steps of:
   a) providing the mouse homozygous for a mutant Col2a-1 gene of claim 1;
   b) obtaining a first measurement of one or more of the cardiac symptoms exhibited by said mouse;
   c) administering an agent to said mouse;
   d) obtaining a second measurement of the cardiac symptoms of step (b) following said administering of an agent; and
   e) comparing the first measurement of step (b) with the second measurement of step (d) in order to determine whether the agent treats one or more of said measured symptoms.

4. The method according to claim 3, wherein the agent is one or more agents that target molecules of the BMP/TGF signaling pathways and the Smad signaling pathways involved in cell hypertrophy.

5. The method according to claim 3, wherein the agent is a naturally occurring compound or a purified derivative thereof, a synthetic compound, a ligand trap, a BMP or TGF agonist, a receptor antagonist, a Smad family protein, or a nucleic acid molecule present in a viral or non-viral vector.

6. A mouse homozygous for a mutated Col2a-1 gene comprising in its genome a homozygous mutation of the Col2a-1 gene, wherein the mutated Col2a-1 gene lacks exon 2 but still comprises the remaining coding sequences of the Col2a-1 gene, wherein said mouse homozygous for the mutated Col2a-1 gene expresses a mutant Col2A-1 protein encoded by the mutant Col2a-1 gene, and displays multiple cardiovascular malformations similar to malformations present in human congenital hear defects, defects in morphogenesis of the heart similar to those associated with a loss of BMP, TGF-beta, and nodal signaling pathways including ventricular septal defect (VSD), patent ductus arteriosus (PDA), persistent truncus arteriosus (PTA), right ventricular hypertrophy, right aortic arch with or without anomalous origins of subclavian arteries, and a double outlet right ventricle (DORV) where aorta and pulmonary arteries arise wholly or in great part from the right ventricle, with associated VSD, transposition of great arteries (TOGA), anomalous coronary arteries, or endocardial cushion defect with primum atrial septal defect.

7. An isolated cell line obtained from heart tissue of the mouse according to claim 6.

* * * * *